(12) United States Patent
Lux et al.

(10) Patent No.: US 9,986,934 B2
(45) Date of Patent: Jun. 5, 2018

(54) MICROWAVE RADAR SENSOR MODULES

(71) Applicant: California Institute of Technology, Pasadena, CA (US)

(72) Inventors: James Paul Lux, Thousand Oaks, CA (US); Richard Kalantar Ohanian, Valley Village, CA (US); Raymond Quintero, Santa Clarita, CA (US); Troy Michael Torrez, Pasadena, CA (US); Keizo Ishikawa, South Pasadena, CA (US); Michael Ray McKee, Lancaster, CA (US); Salman-ul Mohammed Haque, Los Angeles, CA (US); Sarah Holmes, Glendale, CA (US); Carl Spurgers, Rancho Cucamonga, CA (US)

(73) Assignee: California Institute of Technology, Pasadena, CA (US)

( * ) Notice: Subject to any disclaimer, the term of this patent is extended or adjusted under 35 U.S.C. 154(b) by 787 days.

(21) Appl. No.: 14/609,354

(22) Filed: Jan. 29, 2015

(65) Prior Publication Data
US 2015/0208945 A1    Jul. 30, 2015

Related U.S. Application Data

(60) Provisional application No. 61/952,366, filed on Mar. 13, 2014, provisional application No. 61/932,937, filed on Jan. 29, 2014.

(51) Int. Cl.
*A61B 5/05* (2006.01)
*A61B 5/113* (2006.01)
(Continued)

(52) U.S. Cl.
CPC ............ *A61B 5/0507* (2013.01); *A61B 5/113* (2013.01); *A61B 2560/0252* (2013.01)

(58) Field of Classification Search
CPC ................. A61B 5/0507; A61B 5/113; A61B 2560/0252; G01S 13/536; G01S 13/04;
(Continued)

(56) References Cited

U.S. PATENT DOCUMENTS 3,670,327 A * 6/1972 Clare et al. ........... G01S 13/536
4,434,424 A * 2/1984 Old ....................... G01S 7/2813
(Continued)

FOREIGN PATENT DOCUMENTS

JP       09044779 A    2/1997
JP       09304525 A    11/1997
(Continued)

OTHER PUBLICATIONS

Extended European Search Report for European Application No. 14785477.2, Search completed Dec. 22, 2016, dated Jan. 9, 2017, 10 Pgs.
(Continued)

*Primary Examiner* — Bernarr E Gregory
(74) *Attorney, Agent, or Firm* — KPPB LLP

(57) ABSTRACT

Systems and methods for detecting biometrics using microwave radar sensor modules are disclosed. Integrated microwave sensor modules can include a transmitter unit configured to generate at least one continuous wave transmit signal based upon at least one frequency control signal, a receiver unit configured to utilize a cancellation path to cancel contributions to a return signal based upon at least one cancellation path control signal, and a microcontroller unit that includes a processor, a memory containing a microcontroller application, where the microcontroller application configures the processor to generate at least one frequency control signal to generate least one CW transmit signal having a plurality of frequencies, generate at least one cancellation path control signal to automatically adjust the
(Continued)

cancellation path in real time, receive at least one demodulated signal, digitize the at least one demodulated signal, and update the at least one frequency control and cancellation path control signals.

25 Claims, 25 Drawing Sheets

(51) Int. Cl.
  *A61B 5/00* (2006.01)
  *G01S 13/00* (2006.01)
(58) Field of Classification Search
  CPC ........ G01S 13/62; G01S 7/2813; G01S 7/038; G01S 7/292; G01S 7/415
  See application file for complete search history.

(56) References Cited

U.S. PATENT DOCUMENTS

| | | | |
|---|---|---|---|
| 4,958,638 A | 9/1990 | Sharpe et al. | |
| 4,970,519 A * | 11/1990 | Minnis et al. | G01S 7/038 |
| 4,991,165 A * | 2/1991 | Cronyn | G01S 7/038 |
| 5,448,501 A * | 9/1995 | Hablov et al. | A61B 5/0507 |
| 5,507,291 A | 4/1996 | Stirbl et al. | |
| 5,760,687 A | 6/1998 | Cousy et al. | |
| 5,861,021 A | 1/1999 | Thome et al. | |
| 5,904,709 A | 5/1999 | Arndt et al. | |
| 6,026,173 A | 2/2000 | Svenson et al. | |
| 6,031,482 A * | 2/2000 | Lemaitre et al. | G01S 13/04 |
| 6,057,761 A | 5/2000 | Yukl et al. | |
| 6,208,286 B1 | 3/2001 | Rostislavovich et al. | |
| 6,307,475 B1 | 10/2001 | Kelley et al. | |
| 6,313,743 B1 | 11/2001 | Abraham-Fuchs et al. | |
| 6,909,397 B1 | 6/2005 | Greneker, III et al. | |
| 6,927,691 B2 | 8/2005 | Yukl et al. | |
| 7,135,980 B2 | 11/2006 | Moore et al. | |
| 7,199,749 B2 | 4/2007 | Greneker, III et al. | |
| 7,646,830 B1 * | 1/2010 | Weill | G01S 7/292 |
| 7,679,545 B2 | 3/2010 | Rausch et al. | |
| 7,889,053 B2 | 2/2011 | McGrath et al. | |
| 8,378,879 B2 * | 2/2013 | Lewis et al. | G01S 13/62 |
| 8,721,554 B2 * | 5/2014 | Lin et al. | A61B 5/0507 |
| 2002/0138768 A1 | 9/2002 | Murakami | |
| 2003/0081503 A1 | 5/2003 | Barnard et al. | |
| 2003/0130697 A1 | 7/2003 | Halperin et al. | |
| 2003/0135097 A1 | 7/2003 | Wiederhold et al. | |
| 2003/0178034 A1 | 9/2003 | Yuki et al. | |
| 2004/0123667 A1 | 7/2004 | McGrath et al. | |
| 2004/0243299 A1 | 12/2004 | Scaer et al. | |
| 2005/0128124 A1 | 6/2005 | Greneker et al. | |
| 2006/0028369 A1 | 2/2006 | Rausch et al. | |
| 2006/0028389 A1 | 2/2006 | Yukl et al. | |
| 2006/0224046 A1 | 10/2006 | Ramadas et al. | |
| 2007/0066904 A1 | 3/2007 | Wesmann et al. | |
| 2008/0007445 A1 | 1/2008 | Leach et al. | |
| 2008/0045832 A1 | 2/2008 | McGrath et al. | |
| 2008/0074307 A1 * | 3/2008 | Boric-Lubecke et al. | A61B 5/0507 |
| 2009/0146869 A1 | 6/2009 | Dwelly et al. | |
| 2009/0278728 A1 | 11/2009 | Morgan et al. | |
| 2010/0079347 A1 | 4/2010 | Hayes et al. | |
| 2010/0109938 A1 | 5/2010 | Oswald et al. | |
| 2010/0249633 A1 | 9/2010 | Droitcour et al. | |
| 2010/0295718 A1 | 11/2010 | Mohamadi et al. | |
| 2010/0321229 A1 * | 12/2010 | Dwelly et al. | G01S 7/415 |
| 2013/0002434 A1 | 1/2013 | Cuddihy et al. | |
| 2014/0316261 A1 | 10/2014 | Lux et al. | |
| 2015/0223701 A1 | 8/2015 | Ghaemi et al. | |

FOREIGN PATENT DOCUMENTS

| | | |
|---|---|---|
| KR | 20030070315 A | 8/2003 |
| WO | 2007118274 A1 | 10/2007 |
| WO | 2008001092 A2 | 1/2008 |
| WO | 2008054490 A2 | 5/2008 |
| WO | 2008054490 A3 | 7/2008 |
| WO | 2011075639 A1 | 6/2011 |
| WO | 2012055148 A1 | 5/2012 |
| WO | 2012158840 A1 | 11/2012 |
| WO | 2014172668 A1 | 10/2014 |

OTHER PUBLICATIONS

International Preliminary Report on Patentability for International Application PCT/US2007/008340, Report dated Oct. 8, 2008, 4 Pgs.

International Search Report and Written Opinion for International Application PCT/US2010/062036, report completed Aug. 31, 2011, dated Aug. 31, 2011, 6 Pgs.

"Arduino HomePage", Arduino, Feb. 1, 2014, https://web.archive.org/web/20140201142732/https://www.arduino.cc/, 3 pages.

"Autoregressive model", Wikipedia, Dec. 8, 2013, retrieved from https://web.archive.org/web/20150106061833/https://en.wikipedia.org/wiki/Autoregressive_model on Jul. 26, 2017, 9 pages.

"Camero—Step into the known", Camero—Tactical Through-Wall Imaging Solutions, Mar. 28, 2013, retrieved from https://web.archive.org/web/20130328000753/http://www.camero-tech.com/ on Jul. 26, 2017, 1 page.

"EMMDAR (Electro-Magnetic Motion Detection and Ranging)", L3 Communications CyTerra, 2011, retrieved from http://www.cyterra.com/products/emmdar.htm on Jul. 26, 2017.

"Fieldnames", MathWorks, Nov. 28, 2013, https://web.archive.org/web/20131128081202/http://www.mathworks.com/help/matlab/ref/fieldnames.html, 2 pages.

"Least squares", VVikipedia, Jan. 30, 2014, https://web.archive.org/web/20140209133957/https://en.wikipedia.org/wiki/Least_squares on Jul. 26, 2017, 9 pages.

"Str2num", MathWorks, Jul. 17, 2013, retrieved from https://web.archive. org/web/20130717105438/http://www.mathworks.com/help/matlab/ref/str2num.html, 2 pages.

"Teensy USB Development Board", PJRC Store, Feb. 9, 2014, retrieved from https://web.archive.org/web/20140209222648/www.pjrc.com/store/teensy3.html, 1 page.

"Teensyduino", PJRC, Feb. 9, 2014, https://web.archive.org/web/20140209215538/https://www.pjrc.com/teensy/teensyduino.html, 3 pages.

"Textscan", MathWorks, Dec. 19, 2013, retrieved from https://web.archive.org/web/20131219081941/http://www.mathworks.com/help/matlab/ref/textscan.html, 3 pages.

"TiaLinx, Inc.", TiaLinx, Inc., Jul. 15, 2012, retrieved from https://web.archive.org/web/20120715031226/www.tialinx.com/eaglefamily.html on Jul. 26, 2017, 4 pages.

"Tianying-Night Vision", Yiwu TianYing Optical Instrument Co., Limited, Mar. 20, 2013, retrieved from https://web.archive.org/web/20130320184606/http://www.nightvisioncn.com:80/sdp/625512/4/main-3235899/0/Home.html on Jul. 26, 2017, 2 pages.

"Troubleshooting Common Problems", PJRC, Feb. 9, 2014, https://web.archive.org/web/20140209214600/https://www.pjrc.com/teensy/troubleshoot.html, 5 pages.

Chongyu et al., "The design of cancellation unit against radiofrequency interference in life-detection radar", 2010 International Conference on Microwave and Millimeter Wave Technology, May 2010, pp. 1758-1761.

Donelli, M., "A Rescue Radar System for the Detection of Victims Trapped Under Rubble Based on the Independent Component Analysis Algorithm", Progress in Electromagnetics Research M, vol. 19, Jul. 29, 2011, pp. 173-181.

Izadi et al., "Design and Simulation of a Life Detection System Based on Detection of the Heart Beat Using Doppler Frequency", 2006 IEEE International Symposium on Signal Processing and Information Technology, Aug. 27-30 2006, Vancouver, BC, Canada, pp. 685-690.

Jianqi et al., "A New Method for Identifying the Life Parameters via Radar", EURASIP Journal on Advances in Signal Processing, vol. 2007, Article ID 31415, Jan. 30, 2007, 8 pages, doi:10.1155/2007/31415.

(56) References Cited

OTHER PUBLICATIONS

Liu et al., "The Application of the Hilbert-Huang Transform in Through-wall Life Detection with UWB Impulse Radar", Piers Online, vol. 6, No. 7, Jan. 2010, pp. 695-699.
Pieraccini et al., "Detection of Breathing and Heartbeat Through Snow Using a Microwave Transceiver", IEEE Geoscience and Remote Sensing Letters, vol. 5, No. 1, Jan. 2008, pp. 57-59.
Xu et al., "A Novel Method for Automatic Detection of Trapped Victims by Ultrawideband Radar", IEEE Transactions on Geoscience and Remote Sensing, vol. 50, Issue 8, Aug. 2012, pp. 3132-3142.
Zade et al., "A Modern Microwave Life Detection System for Human Being Buried Under Rubble", International Journal of Advanced Engineering Research and Studies, E-ISSN2249-8974, vol. 1, Issue 1, Oct.-Dec. 2011, pp. 69-77.
International Preliminary Report on Patentability for International Application PCT/US2014/034700, dated Oct. 20, 2015, dated Oct. 29, 2015, 5 Pgs.
International Search Report and Written Opinion for International Application PCT/US2014/034700, report completed Sep. 3, 2014, dated Sep. 3, 2014, 7 Pgs., Sep. 3, 2014.
Chen, Kun-Mu et al., "Microwave Life-Detection Systems for Searching Human Subjects Under Earthquake Rubble or Behind Barrier", IEEE Transactions on Biomedical Engineering, Jan. 2000, vol. 27, No. 1, pp. 105-114.
Ghaemi, "Synthetic Aperture Weather Radar", Thesis, 2008, 78 pgs.
Hirsch et al., "Respiratory sinus arrhythmia in humans: how breathing pattern modulates heart rate", American Physiological Society, 1981, pp. H620-H629.
Li et al., "Efficient Mixed-Spectrum Estimation with Applications to Target Feature Extraction", IEEE Transactions on Signal Processing, vol. 44, No. 2, Feb. 1996, 281-295.
Liu et al., "Feature extraction of SAR targets consisting of trihedral and dihedral corner reflectors", IEE Proc.-Radar, Sonar Navig., Jun. 1998, Vo. 145, No. 3, pp. 161-172.

\* cited by examiner

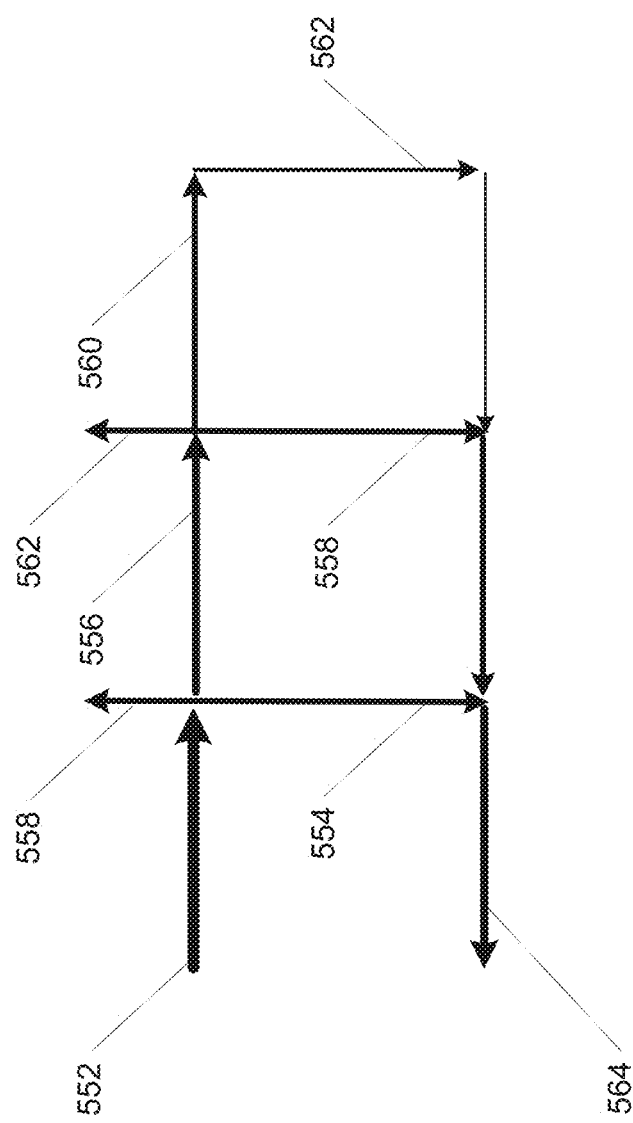

1200

1210

1220

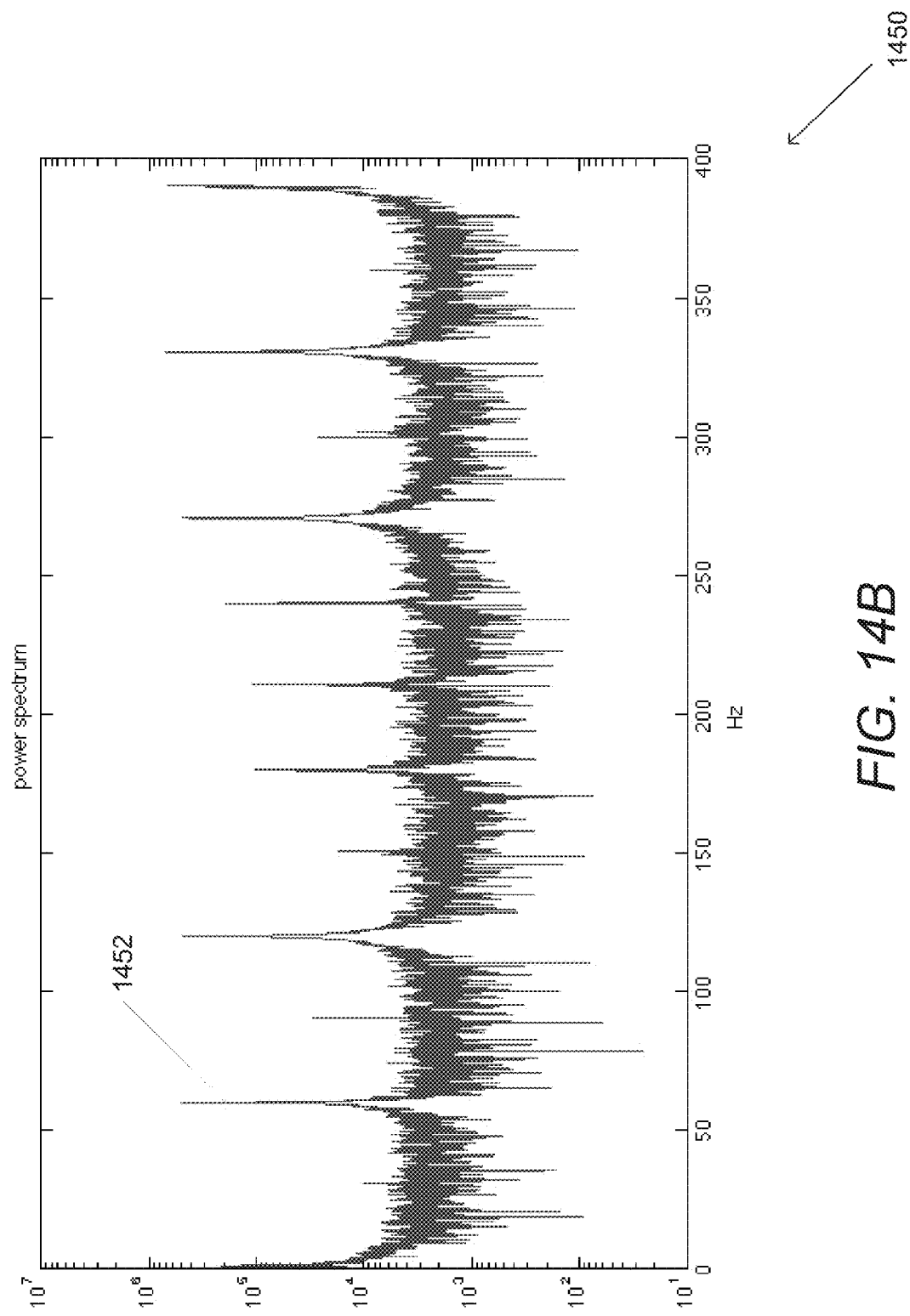

MICROWAVE RADAR SENSOR MODULES

CROSS-REFERENCE TO RELATED APPLICATIONS

The current application claims priority to U.S. Provisional Patent Application Nos. 61/932,937 filed Jan. 29, 2014, and 61/952,366 filed Mar. 13, 2014, the disclosures of which are incorporated herein by reference.

FEDERAL FUNDING SUPPORT

The invention described herein was made in the performance of work under a NASA contract, and is subject to the provisions of Public Law 96-517 (35 USC 202) in which the Contractor has elected to retain title.

FIELD OF THE INVENTION

The present invention generally relates to radars and more specifically to microwave radar sensor modules for systems and methods for detecting biometrics.

BACKGROUND

Biometrics refer to the quantifiable data (or metrics) related to human characteristics and traits. The quantifiable metrics can be gathered using various sensors and the collected data processed to identify individual persons. Typically, biometric identifiers can be categorized as physiological and/or behavioral characteristics. Generally, physiological characteristics are related to the shape of the body and can include (but not limited to) fingerprint, palm print, DNA, and scent. In contrast, behavioral characteristics relate to a pattern of behavior and include (but not limited to) gait, voice, and typing rhythm. Biometric identifiers can also include characteristics that are more subtle such as breathing patterns and heart rates.

SUMMARY OF THE INVENTION

Systems and methods for detecting biometrics using microwave radar sensor modules in accordance with embodiments of the invention are disclosed. In one embodiment, an integrated microwave sensor module includes a transmitter unit that includes a variable frequency microwave source connected to at least one transmitter unit amplifier, where: the variable frequency microwave source is configured to generate at least one continuous wave ("CW") transmit signal based upon at least one frequency control signal received from a microcontroller unit, and the at least one transmitter unit amplifier is configured to receive and amplify the at least one CW transit signal; a receiver unit configured to receive at least one return signal and utilize a cancellation path to cancel contributions to the return signal that are not the result of reflections from a target that includes a vector modulator, a combiner, a vector demodulator, and at least one receiver unit amplifier, where: the vector modulator is configured to receive at least one cancellation path control signal from the microcontroller unit, sample the at least one CW transmit signal, and adjust an amplitude and phase of the sampled CW transmit signal based upon the at least one cancellation path control signal, the combiner is configured to receive the adjusted transmit signal and combine it with the at least one return signal, the at least one receiver unit amplifier is configured to amplify the combined signal, and the vector demodulator is configured to receive the amplified combined signal, sample the at least one CW transmit signal, and generate two baseband signals by coherently demodulating the amplified combined signal using the sampled CW transmit signal; a microcontroller unit configured to communicate with the transmitter and receiver units that includes: a processor, a memory containing a microcontroller application, where the microcontroller application configures the processor to: generate at least one frequency control signal, wherein the at least one frequency control signal can configure the transmitter unit to generate least one CW transmit signal having a plurality of frequencies, generate at least one cancellation path control signal, wherein the at least one cancellation path control signal can configure the receiver unit to automatically adjust the cancellation path in real time, receive at least one demodulated signal from the receiver unit; digitize the at least one demodulated signal, and update the at least one frequency control and cancellation path control signals based upon the received at least one demodulated signal.

In a further embodiment, the variable frequency microwave source is a voltage controlled oscillator.

In another embodiment, the at least one transmitter unit amplifier is connected to at least one transmit antenna configured to propagate at least one beam using the amplified CW transmit signal set at a plurality of frequencies.

In a still further embodiment, the at least one return signal is associated with reflections from objects of the at least one beam, where the return signal comprises at least one signal component having a static phase associated with reflections from nonmoving objects and at least one signal component having time varying phase associated with at least one target.

In still another embodiment, the microcontroller application also configures the processor to automatically adjust cancellation paths associated with each of the plurality of frequencies.

In a yet further embodiment, the microcontroller unit also includes at least one digital-to-analog converter for processing the at least one transmitter frequency control signal.

In yet another embodiment, the microcontroller unit also includes a plurality of digital-to-analog converters for processing the at least one cancellation path control signal.

In a further embodiment again, the receiver unit also includes a low pass filter to filter the demodulated signal.

In another embodiment again, the microcontroller unit also includes a plurality of analog-to-digital converters that digitizes the at least one demodulated signal received from the receiver unit.

In a further additional embodiment, the microcontroller unit is connected to a host computer.

In another additional embodiment, the microcontroller unit also includes a temperature sensor configured to take a temperature measurement related to the sensor module.

In a still yet further embodiment, the microcontroller application also configures the processor to generate an updated frequency control signal based upon the temperature measurement.

In still yet another embodiment, the microcontroller application also configures the processor to generate an updated cancellation path control signal based upon the temperature measurement, wherein the temperature measurement can provide an a priori starting point for adjusting the cancellation path.

In a still further embodiment again, the microcontroller application also configures the processor to validate the demodulated signals and format for further processing.

In still another embodiment again, the microcontroller application also configures the processor to provide range resolution by processing time and frequency measurements.

In a still further additional embodiment, the transmitter unit is implemented on a first printed-circuit-board ("PCB"), the receiver unit is implemented on a second PCB, and the microcontroller unit is implemented on a third PCB.

In still another additional embodiment, the transmitter and receiver units are separate and synchronized.

In a yet further embodiment again, the integrated microwave sensor module is synchronized with another integrated microwave sensor module.

In yet another embodiment again, the integrated microwave sensor module, also includes N transmitter units, M receive antennas, and N×M receiver units to simultaneously processes multiple frequencies.

In a yet further additional embodiment, the vector modulator can be an alternate discrete implementation that includes a quadrature hybrid coupler, a first and second discrete mixers, and a power combiner.

In yet another additional embodiment, the quadrature hybrid coupler receives a sampled CW transmit signal from the transmitter unit and splits the received sampled CW transmit signal into a first and second split signals that are 90 degrees apart in phase.

In a further additional embodiment again, the first discrete mixer is configured to receive the first split signal and a first input control signal and output a first mixer signal.

In another additional embodiment again, the second discrete mixer is configured to receive the second split signal and a second input control signal and output a second mixer signal.

In a still yet further embodiment again, the first and second mixer signals are combined using the power combiner to generate a cancellation signal.

In still yet another embodiment again, an integrated microwave sensor module includes a transmitter unit that includes a voltage controller oscillator ("VCO") connected to at least one transmitter unit amplifier, where: the VCO is configured to generate at least one continuous wave ("CW") transmit signal based upon at least one frequency control signal received from a microcontroller unit, the at least one transmitter unit amplifier is configured to receive and amplify the at least one CW transit signal, and the at least one transmitter unit amplifier is connected to at least one transmit antenna configured to propagate at least one beam using the amplified CW transmit signal set at a plurality of frequencies based upon the at least one frequency control signal; a receiver unit configured to receive at least one return signal and utilize a cancellation path to cancel contributions to the return signal that are not the result of reflections from a target comprising a vector modulator, a combiner, a vector demodulator, and at least one receiver unit amplifier, where: the vector modulator is configured to receive at least one cancellation path control signal from the microcontroller unit, sample the at least one CW transmit signal, and adjust an amplitude and phase of the sampled CW transmit signal based upon the at least one cancellation path control signal, the combiner is configured to receive the adjusted transmit signal and combine it with the at least one return signal, the at least one receiver unit amplifier is configured to amplify the combined signal; and the vector demodulator is configured to receive the amplified combined signal, sample the at least one CW transmit signal, and generate two baseband signals by coherently demodulating the amplified combined signal using the sampled CW transmit signal, and the at least one return signal is associated with reflections from objects of the at least one beam, where the return signal comprises at least one signal component having a static phase associated with reflections from non-moving objects and at least one signal component having time varying phase associated with at least one target; a microcontroller unit configured to communicate with the transmitter and receiver units includes: a processor, a memory containing a microcontroller application, where the microcontroller application configures the processor to: generate at least one frequency control signal, where the at least one frequency control signal can configure the transmitter unit to generate least one CW transmit signal having a plurality of frequencies, generate at least one cancellation path control signal, where the at least one cancellation path control signal can configure the receiver unit to automatically adjust the cancellation path in real time, receive at least one demodulated signal from the receiver unit, digitize the at least one demodulated signal, and update the at least one frequency control and cancellation path control signals based upon the received at least one demodulated signal, at least one digital-to-analog converter for processing the at least one transmitter frequency control signal, a plurality of digital-to-analog converters for processing the at least one cancellation path control signal, and a plurality of analog-to-digital converters that digitizes the at least one demodulated signal received from the receiver unit.

BRIEF DESCRIPTION OF THE DRAWINGS

FIGS. 5A and 5B illustrate signal propagation characteristics of a signal generated by a FINDER system in accordance with an embodiment of the invention.

FIGS. 14A and 14B are spectrograms illustrating data collected using a sensor module in fluorescent lighting conditions in accordance with an embodiment of the invention.

DETAILED DESCRIPTION OF THE DRAWINGS

Turning now to the drawings, integrated microwave sensor modules for detecting biometrics such as (but not limited to) heartbeat and breathing in accordance with embodiments of the invention are disclosed. In many embodiments, the sensor module integrates a microcontroller unit with transmitter and receiver units for target detection and/or biometric measurements. In various embodiments, the transmitter unit can include at least one transmit antenna that transmits a continuous microwave (CW) signal at various frequencies to illuminate at least one sensing area. In several embodiments, the receiver unit can include at least one receive antenna configured to receive a return signal associated with reflections of the transmitted signal from various objects and/or targets. Typically, the transmitted signal is used as a reference for the demodulation of the received signal. Typically, the receiver unit coherently combines an amplitude and phase adjusted sample of the transmitted signal with the received signal to cancel contributions to the received signal that are not the result of reflections from the target. As discussed further below, the microcontroller unit can be configured using software to calibrate and initialize various parameters including (but not limited to) the transmit frequencies and cancellation paths using automated processes. In various embodiments, the sensor module can also include an external synchronization interface allowing multiple sensor modules to interconnect and be simultaneously sampled so that multiple sensors can be utilized to detect a one or more targets and also measure biometrics.

Although sensor modules for use in Life Detecting Radar (FINDER) Systems are described in detail below as applied to detecting victims buried in rubble, it can have various other applications including (but not limited to) detecting prisoners barricaded in a prison, suspects hiding in farm fields or houses, general motion detection, species identification, as well being used as a form of diagnostic or biometric measurement instrument. Finder systems for detecting biometrics of and/or identifying a target in accordance with embodiments of the invention are further discussed below.

Life Detecting Radar ("FINDER") Systems

Figure 1:
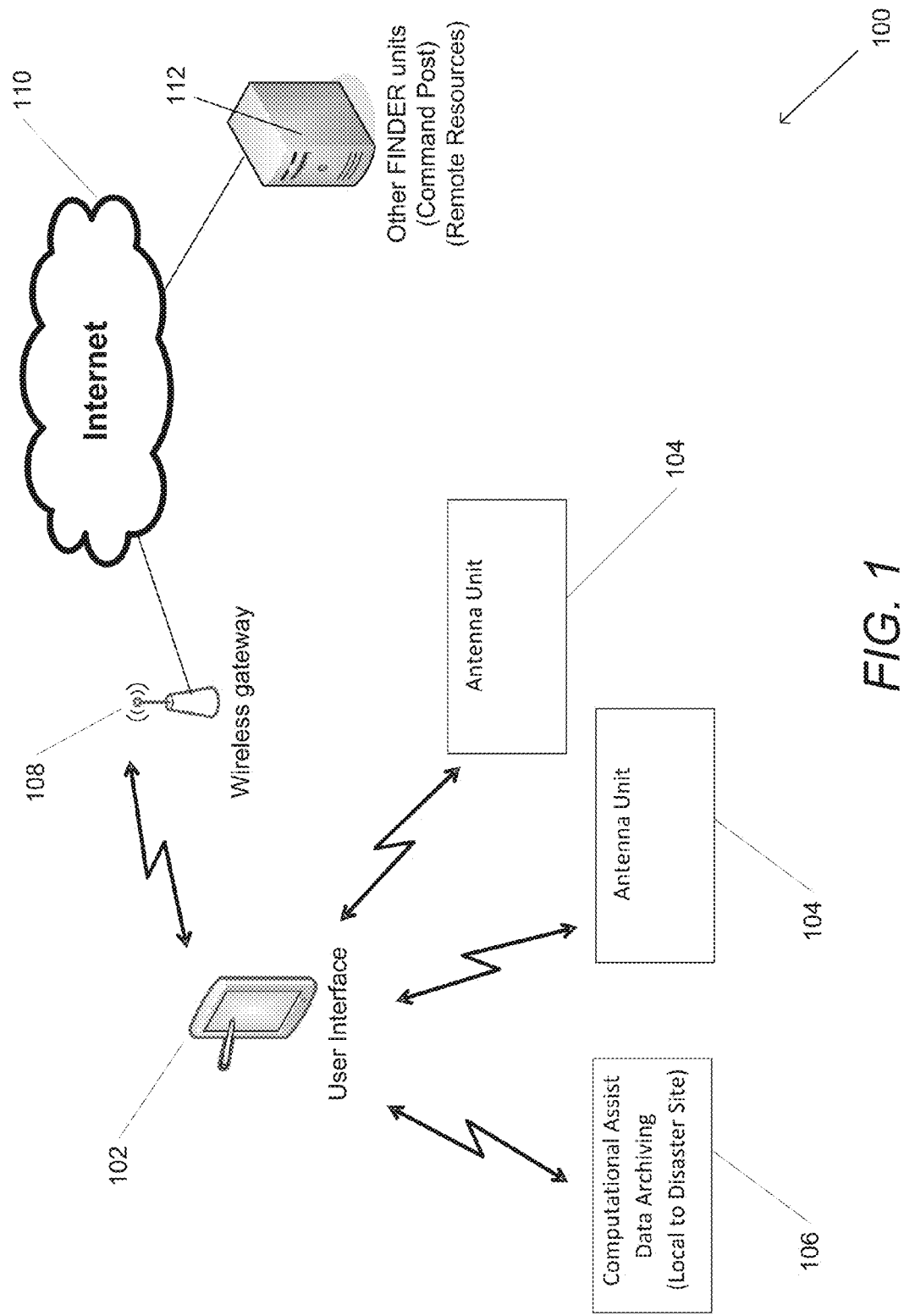
FIG. 1 is a system diagram of a life detecting radar ("FINDER") in accordance with an embodiment of the invention.

FINDER (acronym for Finding Individuals for Disaster and Emergency Response) systems can be utilized to detect biometrics (i.e. physiological characteristics) of various targets. A FINDER system in accordance with an embodiment of the invention is illustrated in FIG. 1. The system 100 includes a user interface 102 configured to wirelessly connect and control at least one antenna unit 104, where the antenna unit transmits and receives radio signals as further described below. In several embodiments, the user interface 102 can also wirelessly connect to various other units including (but not limited to) computational assist units and data archiving units 106. In many embodiments, the user interface 102 can communicate wirelessly with a cellular data network 108 (i.e. wireless gateway) to connect to the Internet 110. Utilizing the Internet 110, the user interface 102 can access additional units including (but not limited to) a command post and other remote resources 112. Although described as separate units, in a variety of embodiments, the user interface 102 and the various units 104, 106 can be one physical unit communicating with each other via a direct network link or other means of data communication.

Figure 2:
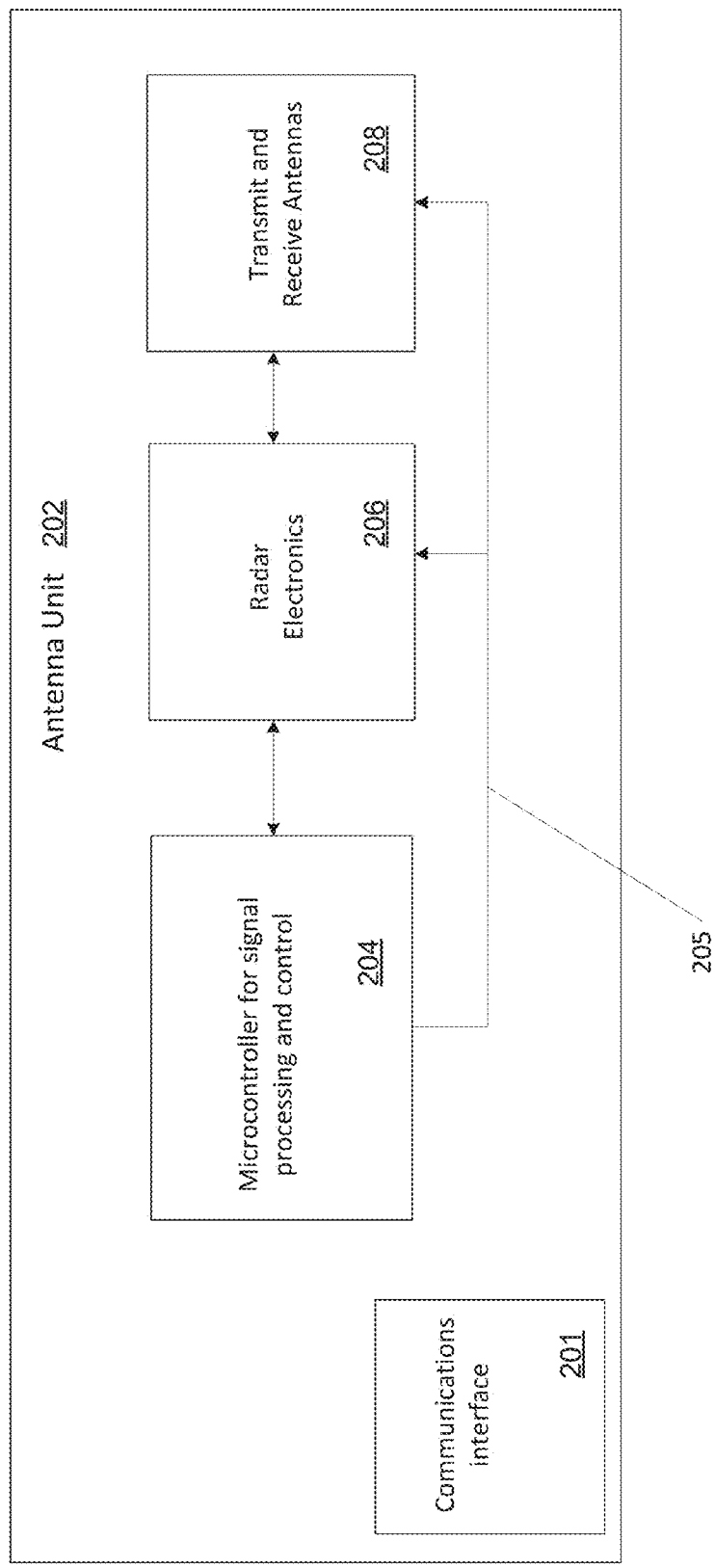
FIG. 2 illustrates an antenna unit in accordance with an embodiment of the invention.

As described above, a FINDER system can include one or more antenna units configured to transmit radio signals including (but not limited to) continuous wave signals and to receive reflected return signals. An antenna unit in accordance with an embodiment of the invention is illustrated in FIG. 2. The antenna unit 202 includes a microcontroller (and/or an embedded PC) 204 that can send control signals 205 to radar electronics 206 and antennas 208 in connection with the microcontroller 204. In various embodiments, the radar electronics themselves can be microcontrollers. In additional embodiments, radar electronics 206 can be incorporated with the transmit antenna 208 (i.e. transmit module). Likewise, radar electronics 206 can be incorporated with the receive antenna 208 (i.e. receive module). In several embodiments, a communications interface 201 can be used to send and receive information or communicate with other antenna units. Communications interface 201 may be wired or wireless. In many embodiments, the antennas 208 include transmit antennas for transmitting radio signals as further discussed below. The antennas 208 can also include receive antennas for receiving return signals that include reflections from various physical objects in the search area as further discussed below. In various embodiments, the received signal is stored as digital radar data and transmitted to the microcontroller (and/or an embedded PC) 204 for signal processing as further discussed below.

Figure 3A:
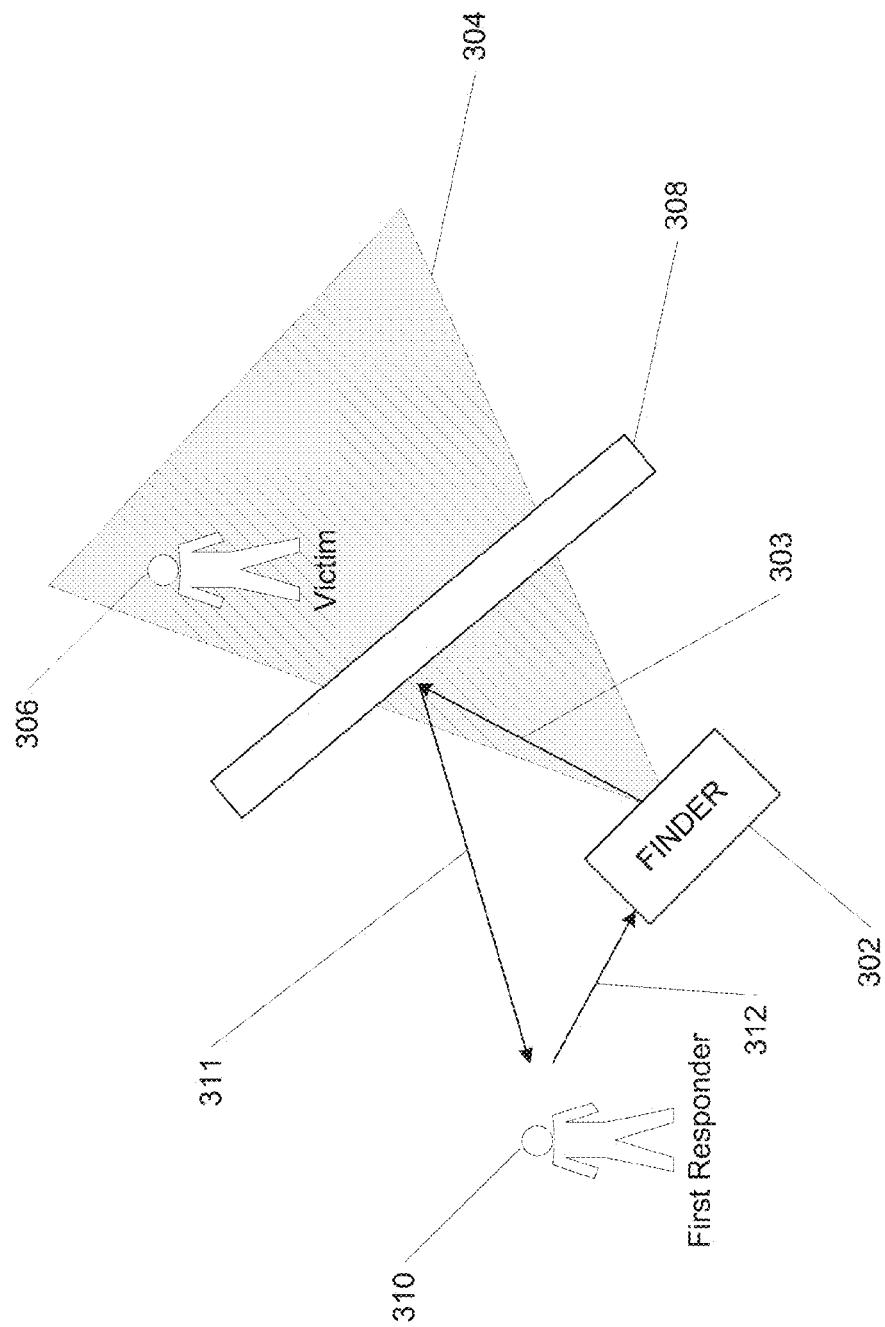
FIG. 3A illustrates a FINDER utilizing a single beam for detection and a reflection of heartbeat signals from a bystander in accordance with an embodiment of the invention.

The ability for a FINDER system to form multiple beams can improve target identification and separation. A FINDER system utilizing a single beam for detection in accordance with an embodiment of the invention is illustrated in FIG. 3A. The FINDER system 302 transmits signals to illuminate a single beam 304 to detect a victim 306 who is surrounded by rubble. Often in real life search scenarios, various objects 308 reflect the transmit signal 303 in undesired directions resulting in unwanted return signals. Further, search personnel ("first responders") 310 can also cause return signals 312 and be misidentified as victims. As illustrated, the transmitted signal 303 is reflecting off various objections 308, and then that reflection 311 is reflecting off the bystander 310, eventually ending up at the FINDER 302. In many embodiments, the beam is not ideal with sharp edges meaning even though the beam 304 is generally directed in a particular direction, signals will be transmitted and received in all directions, at reduced amplitudes.

Figure 3B:
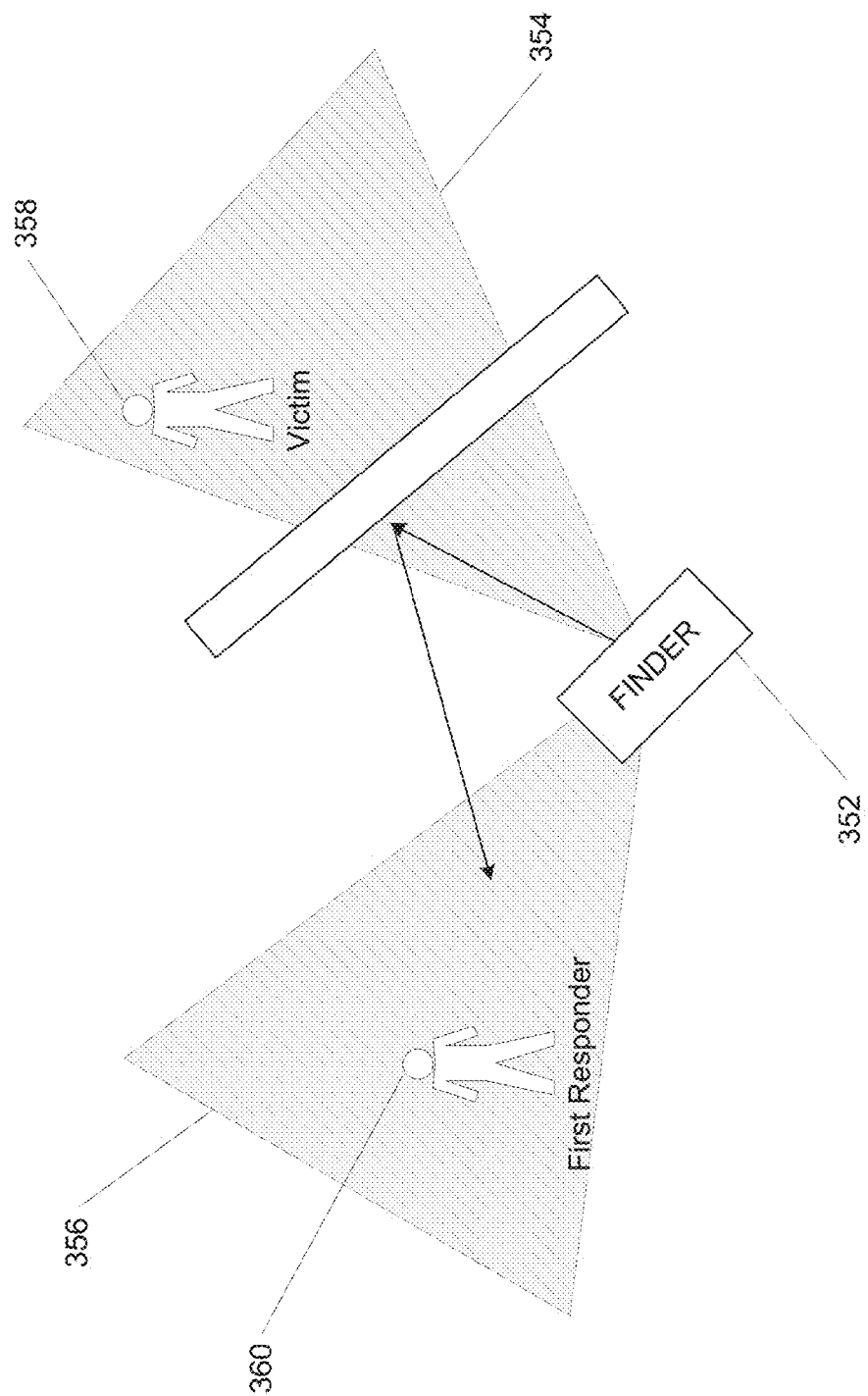
FIG. 3B illustrates a FINDER utilizing multiple beams for detection and elimination of a bystander target in accordance with an embodiment of the invention.

The use of multiple beams can increase detection accuracy and sensitivity. A FINDER system utilizing multiple beams for detection in accordance with an embodiment of the invention is illustrated in FIG. 3B. The FINDER 352 can form multiple beams 354 and 356 as further discussed below. The first beam 354 can detect the victim 358 while the second beam 356 can eliminate the first responder 360 as a possible victim as further discussed below. In addition, the ability to simultaneously "view" the search area in multiple directions can be useful. For example, being able to look in multiple directions at the same time allows rejection of phantom victims in the search area that are really just reflections from someone standing behind the FINDER antenna unit or next to the search area. In many embodiments, FINDER systems can be designed such that the basic radio frequency ("RF") signal chain is readily scalable to multiple beams and locations.

Figure 4A:
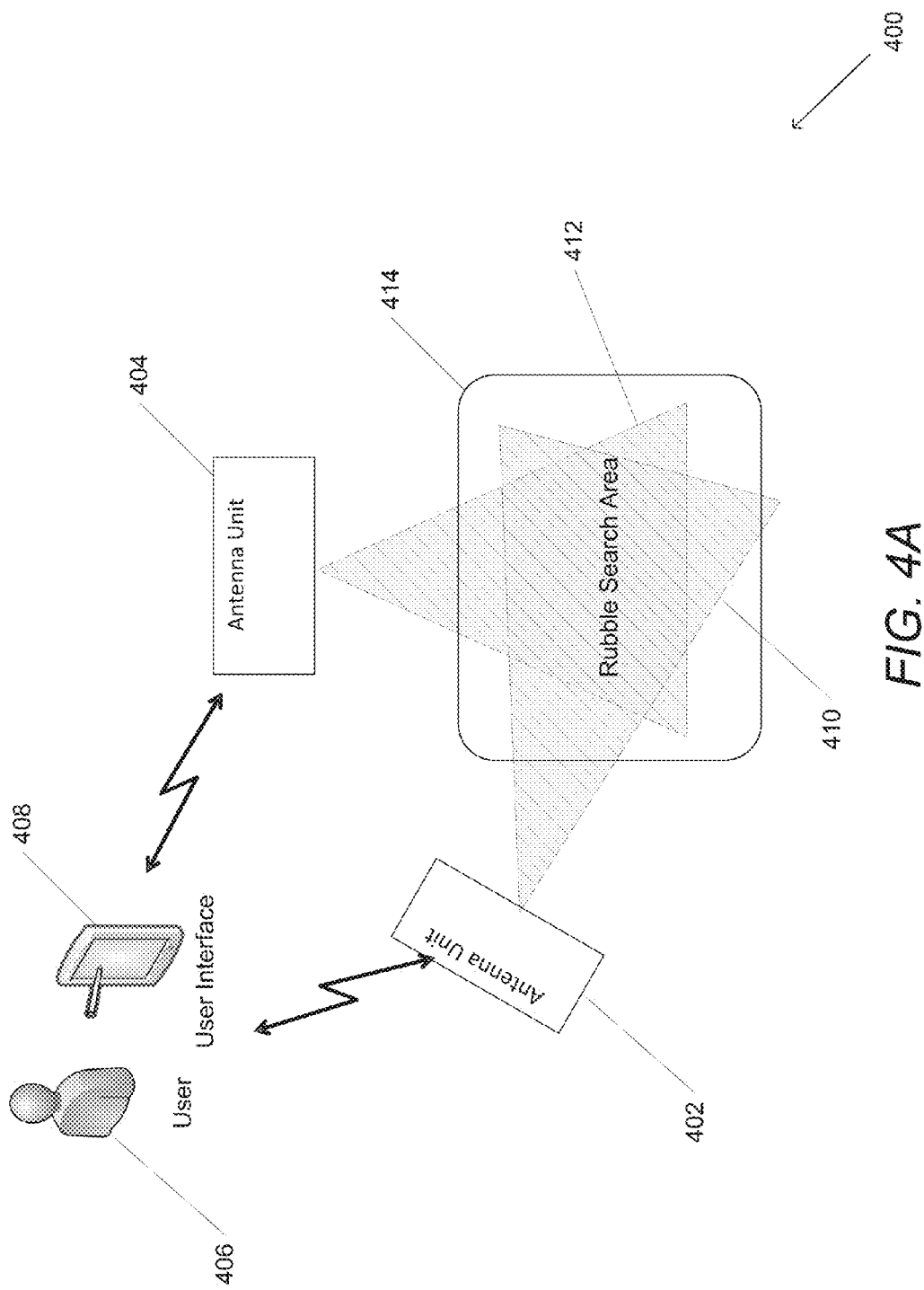
FIGS. 4A and 4B illustrate FINDER systems utilizing multiple Antenna Units in accordance with an embodiment of the invention.
Figure 4B:
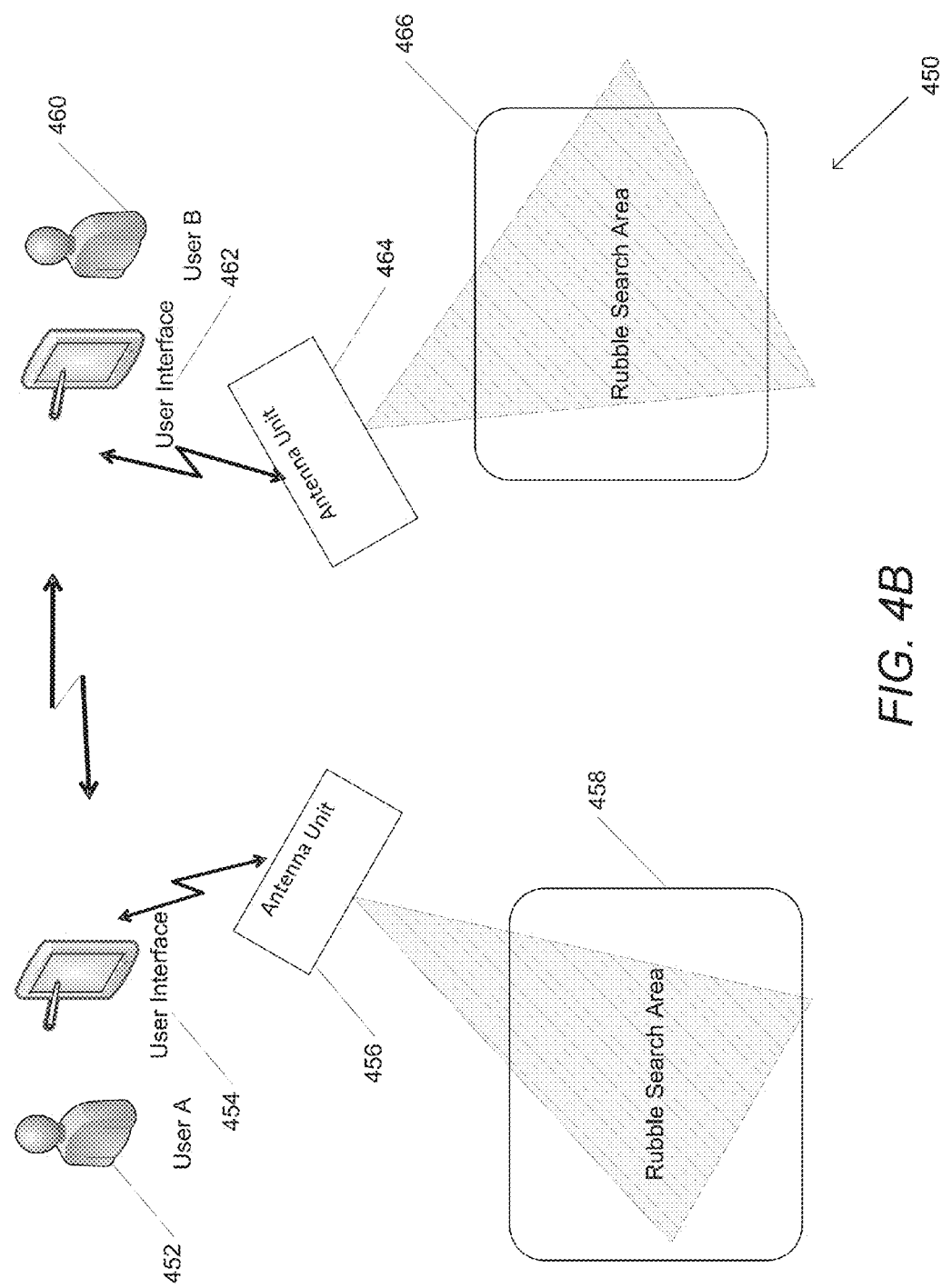

In addition to multiple beams, FINDER systems can utilize multiple frequencies in an allocated bandwidth. A FINDER system employing multiple frequencies can avoid interference by signals from other sources and/or not interfere with other systems by using a different frequency from such other systems. The use of multiple frequencies in accordance with an embodiment of the invention is illustrated in FIGS. 4A-B. The search scenario 400 illustrates two antenna units 402 and 404 being controlled by a single user 406 via a single user interface 408. The antenna unit 402 transmits a transmit signal to illuminate a beam 410 at a first frequency while antenna unit 404 transmits a separate transmit signal to illuminate a second beam 412 at a second frequency. Both beams 410 and 412 are transmitted to the same rubble search area 414 without interfering with each other because the two transmit signals operate at different frequencies. FINDER systems utilizing multiple frequencies to illuminate two separate rubble search areas at the same location in accordance with an embodiment of the invention is illustrated in FIG. 4B. The search scenario 450 illustrates User A 452 utilizing a user interface 454 that communicates with an antenna unit 456 to illuminate a rubble search area 458 utilizing a first frequency. At the same location, User B 460 can utilize a user interface 462 to communicate with an antenna unit 464 to illuminate a rubble search area 466 using a second frequency. Again, the use of multiple frequencies allow for the FINDER systems to avoid interfering with each other while operating in the same location. Furthermore, the detection of victims or targets can be enhanced by combining the outputs of multiple FINDER systems to collect data concerning a target from multiple directions. In several embodiments, synchronized data recording can be utilized to enable the detection of matching time varying signals such as (but not limited to) respirations and heart beats in signals received by different antennas and/or FINDER systems.

Although specific FINDER systems for detecting victims are discussed above with respect to FIGS. 1-4B, any of a variety of FINDER systems for detecting victims as appropriate to the requirements of a specific application can be utilized in accordance with embodiments of the invention. Signal processing for victim detection in accordance with embodiments of the invention are discussed further below.

Signal Characteristics and Signal Processing

FINDER systems utilize the principle of looking for small phase changes in a CW signal reflected from a victim due to motion or internal changes. As a victim breathes, their body moves slightly (in particular, their chest wall on the order of 1 cm), and similarly, their heartbeat causes the abdominal surface and many other portions of the human body to move (on the order of 1 mm). The moving body causes reflections of transmit signals with varying phases (i.e. phase change). The detected phase change by receive antennas forms the basis of the so-called microwave cardiogram ("MCG").

Typically, each person has a unique MCG which varies depending on their orientation relative to the sensor, and, their physiological state. The uniqueness of MCG allows for the separation of combined MCGs from multiple targets (statistical analysis shows that it is unlikely that two people would have exactly the same heart rate, and even if the average rate were the same, the beat to beat variability is a random process, causing the two sequences to be uncorrelated). However, in real search scenario, there may be a multitude of other objects besides the victim reflecting a microwave signal back to the receiver, including (but not limited to) the rubble surrounding the victim, and objects near the radar. Typically, such signals are reflected from objects that are not moving and thus the phase stays relatively constant/static. The return signal that a radar receiver detects is typically a combination of a strong static signal component (corresponding to reflections from non-moving objects) that is unchanging with a weaker time varying signal component (corresponding to a victim). In terms of level, the static signal component that is received by the radar is typically on the order of 20 dB weaker than the transmitted signal, while the time varying return signal reflected off a victim is typically 60-100 dB (or more) weaker. The dominant reason for the weaker signal from the victim is the scattering of the signal in the rubble, as well as the bulk attenuation in the rubble material.

Figure 5A:
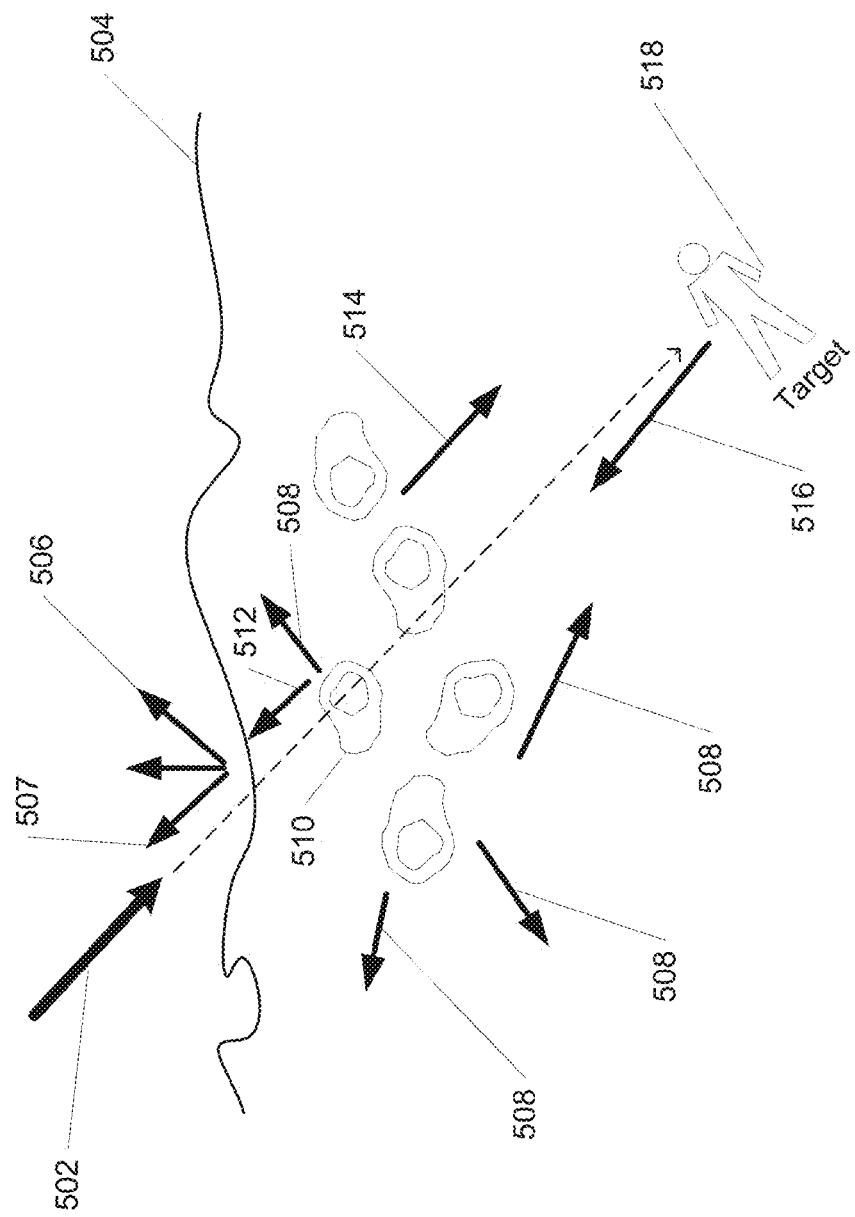

Signal propagation characteristics in accordance with an embodiment of the invention are illustrated in FIGS. 5A-B. In many embodiments, a transmit signal 502 in a frequency band such as (but not limited to) 3.1-3.4 GHz can hit a surface 504 causing surface scatter with portions that scatter away 506 and portions that reflect back 507 to the radar. In several embodiments, portions of the transmit signal (and any reflected signals) can be absorbed and lost into the soil 508. Further, rubble 510 can cause rubble scatter, again, with portions reflecting back toward the radar 512, portions directing toward the target 514, and portions that scattered away. A buried target 518 can also cause a target reflection that includes portions that reflect toward the radar 516, portions that are loss due to soil absorption, and/or scatter away. FIG. 5B illustrates the cumulative effects of reflections of a transmitted signal. The transmitted signal 552 first hits a surface causing surface scatter back toward the radar 554, toward the target 556, and away 558. Rubble in the search area can cause rubble scatter toward the radar 558, toward the target 560, and away 562. Further, a target causes a target reflection toward the radar 562. The cumulative signal of the reflections back towards the radar is received by a receive antenna at the received signal 564. Generally, portions of all signals (signals that return toward the radar or continue towards the victim) can be lost to the soil and/or scattered away.

In many embodiments, contributions to the received signal that are not the result of target reflections can be characterized as clutter and removed via a cancellation path. In various embodiments, the cancellation path includes subtracting a sample of the transmitted signal from the received signal where the sample signal's phase and amplitude are adjusted to closely match the static unvarying clutter signal. In many embodiments, the transmitted signal that is cancelled from the received signal is not the signal actually transmitted by the finder system, but can be a signal received by the finder system from a direction that does not include the search area. Therefore, the transmitted signal can be considered to be any signal that enables cancellation of environmental reflections from areas outside of the search area. Typically, when the sample signal is subtracted from the received signal, only a varying signal from the victim(s) remains and can be further processed for biometric analysis and victim detection. In several embodiments, the cancellation path can be automatically adjusted utilizing software as further described below.

Although specific signal characteristics and signal processing methods for detecting victims are discussed above with respect to FIGS. 5A-B, any of a variety of signals and processing of signals for detecting victims as appropriate to the requirements of a specific application can be utilized in accordance with embodiments of the invention. FINDER systems capable of discriminating between spurious and intended targets in accordance with embodiments of the invention are discussed further below.

Target Separation

Spurious targets (i.e. not intended targets) can be a problem in detecting victims in a search area. As discussed above, a person standing to the side of the search area can show up as a target, because the antenna's response does not fall off very quickly. Typically, spurious targets show up as a very strong signal because their reflection are not attenuated and scattered by passing through the rubble. In many embodiments, multiple beams can be utilized to simultaneously look in multiple directions, including to the side and rear of a FINDER. Further, a target that is not within the sensing area of a particular receive antenna may be detected by other receive antennas, and may even produce a stronger reflection signal in those directions allowing it to be identified and separated out. Likewise, multiple frequencies can be useful as reflected and side targets tend not to be as scattered and thus showing up as narrower time domain responses. In addition, a FINDER system can divide a search area into multiple sensing areas in different directions and distances.

Figure 6:
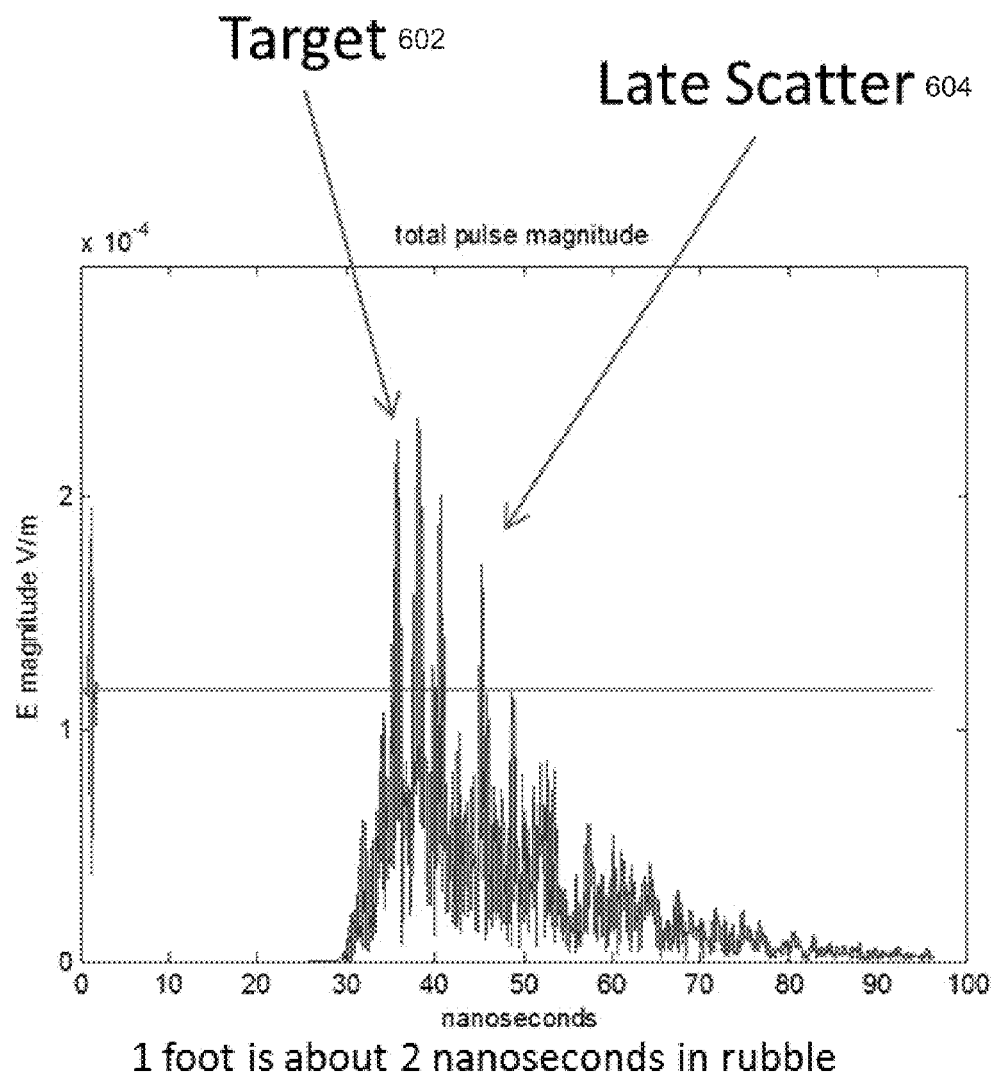
FIG. 6 is a graph illustrating the calculated time domain response of a received signal in accordance with an embodiment of the invention.

A graph illustrating a calculated time domain response in accordance with an embodiment of the invention is illustrated in FIG. 6. The graph 600 depicts spikes of magnitude at various times corresponding to reflections from a target 602 and late scatter 604. In many embodiments, a two nanosecond delay corresponds to one foot of rubble. Further, the graph demonstrates that there can be limits to the position accuracy of the radar.

Figure 7:
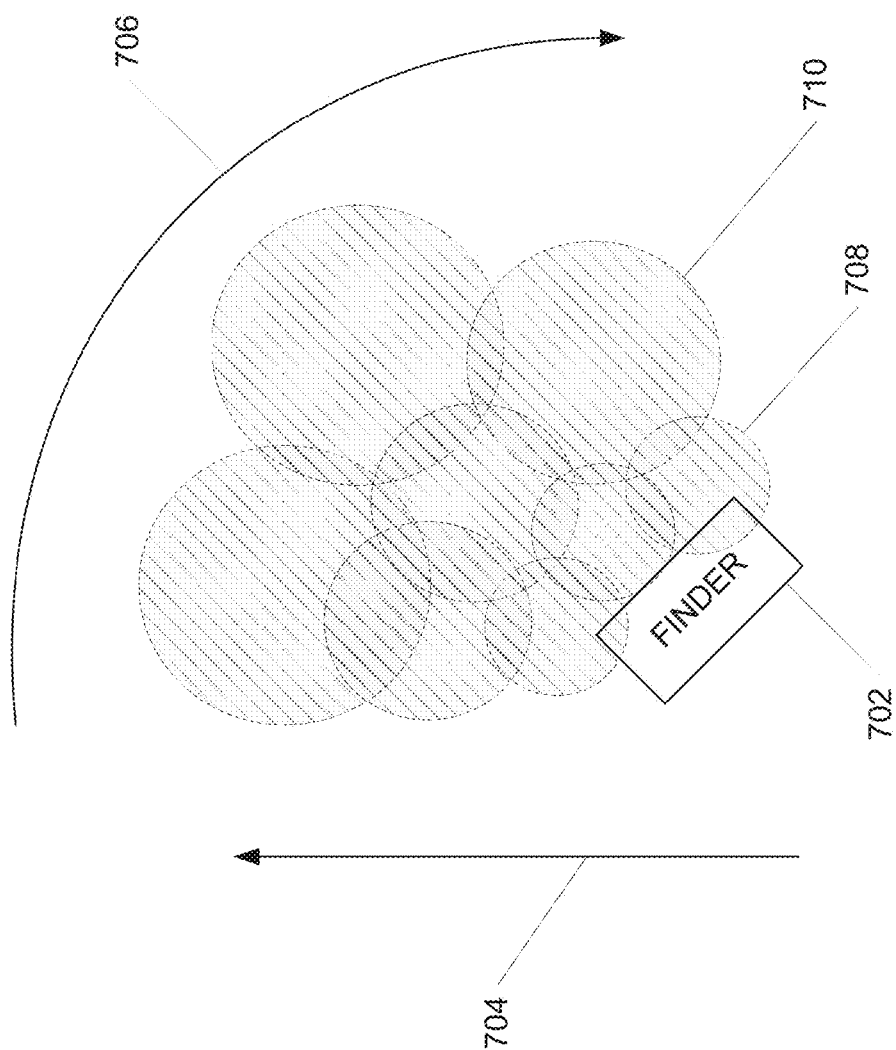
FIG. 7 illustrates sensing areas of a FINDER system in accordance with an embodiment of the invention.

Various sensing areas in accordance with an embodiment of the invention are illustrated in FIG. 7. The FINDER system 702 can have a range 704 and sweeping direction 706 defining different sensing areas such as 708 and 710. Typically, targets will show up in multiple sensing areas, but will be stronger or more sharply defined in some areas than in others. In processing the received signals, the sensing areas directly in front of the FINDER system and the targets which have levels and characteristics consistent with being the intended target can be presented to a user. In many embodiments, the FINDER uses multiple antennas for multiple beams and a limited stepped frequency CW radar techniques for multiple range zones. In various embodiments, the size of the zones can be configured based upon the data utilized to calculate the time domain response.

Figure 8:
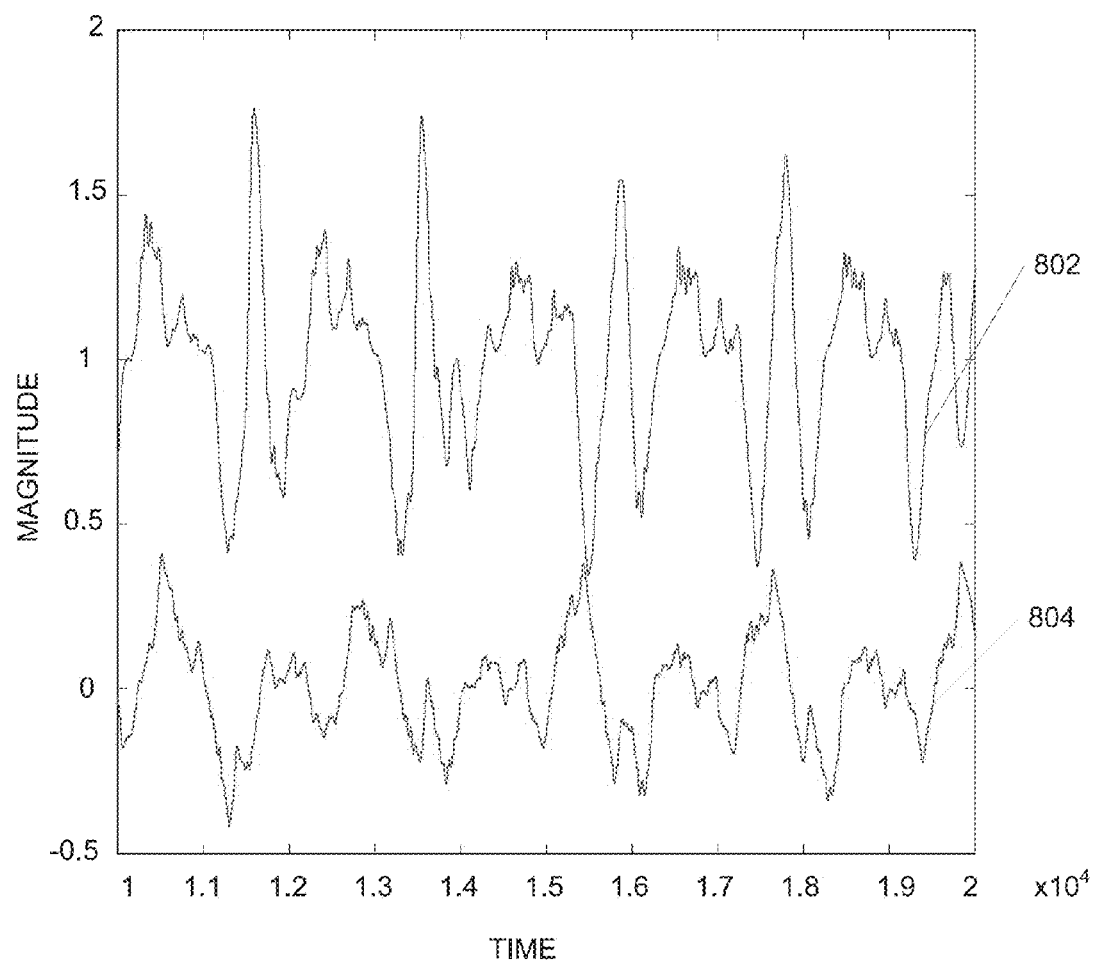
FIG. 8 is a graph illustrating microwave cardiogram ("MCG") recorded from two subjects in accordance with an embodiment of the invention.

The FINDER system can also discriminate among targets since each person typically has a unique MCG and respiration related reflection signals. A graph illustrating MCG recorded from two subjects in accordance with an embodiment of the invention is illustrated in FIG. 8. The graph 800 shows approximately 10 seconds of MCGs recorded from two different subjects. While both the first signal 802 and the second signal 804 are rhythmic and periodic, both signals are quite different and readily distinguishable.

Although specific target discrimination techniques utilizing multiple sensing areas are discussed above with respect to FIGS. 6-8, any of a variety of target discrimination techniques utilizing multiple sensing areas as appropriate to the requirements of a specific application can be utilized in accordance with embodiments of the invention. Radio Frequency ("RF") Modules for victim detection in accordance with embodiments of the invention are further discussed below.

RF Modules

Typically, an RF module is a small electronic device used to transmit and/or receive radio signals. RF modules can be configured (and include components) to perform transmit (i.e. transmitter module), receive (i.e. receiver module), or combination of transmitter and receiver functions. In many embodiments, the FINDER system can be configured such that the RF module is a single channel and single beam CW FM radar.

Figure 9:
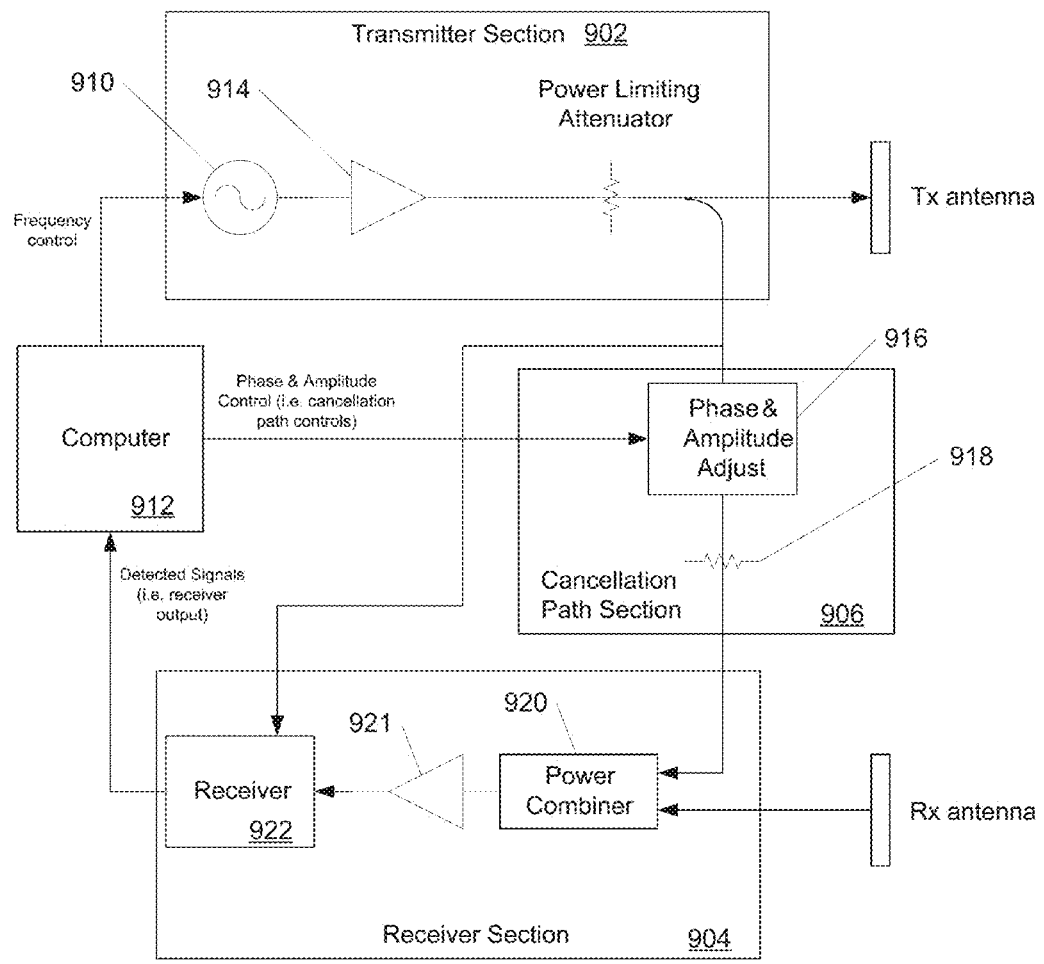
FIG. 9 is a block diagram illustrating a combined Radio Frequency ("RF") module in accordance with an embodiment of the invention.

A combined RF module in accordance with an embodiment of the invention is illustrated in FIG. 9. The RF module 900 can be divided into three sections: a transmitter section 902 which generates the variable frequency signal radiated towards the rubble; a receiver section 904 which demodulates the signals reflected from the rubble (and victim); and the cancellation path section 906 which is used to cancel out the unchanging response (i.e. clutter), leaving just the changing signal (i.e. target reflection). The RF module can also include frequency controls, cancellation path controls (as two signals, I and Q), and receiver output (as two signals, I and Q). In many embodiments, the transmitter section includes a variable frequency microwave source where a Voltage Controlled Oscillator ("VCO") 910 is driven by a digital-to-analog converter ("DAC") controlled by a computer 912 to set frequencies for transmit signals. The VCO output is followed by filters and buffer amplifiers 914 resulting in a 1-10 mW signal. The transmitter section can also include power dividers that take a coherent sample of the transmitted signal where the sample signal can be used for the cancellation signal and to set the local oscillator for the receiver's demodulator. In many embodiments, the cancellation path section can use an I/Q vector modulator 916 to adjust the amplitude and phase 916 of the cancellation signal. The I/Q inputs can be driven from DACs in the digital module, which are controlled by the computer to optimally cancel the fixed clutter signal. Any gain or offset imbalance in the I/Q inputs can be compensated by adjusting the DACs in a closed loop process. Since the control signals are essentially direct current ("DC") signals, any phase imbalance in the control paths would manifest as something that can be controlled by the gain and offset. In several embodiments, the cancellation path includes a 20 dB attenuator 918 to move the adjustment range closer to the expected level of the clutter signal. The value of the attenuator can be adjusted for optimum performance. In various embodiments, resistive voltage dividers can be used to scale the output of the DAC to appropriate levels for the vector modulator.

In several embodiments, the receiver section 904 of the RF module can include a bandpass filter to select frequencies utilized by the radar and to remove the unwanted signals from adjacent bands. The demodulator is essentially a direct conversion to baseband, so out of band image responses are not a concern, however there can be about 50 dB of gain in the receiver before the demodulation and so filtering avoids amplifying any out of band signals. After the initial filtering, the received signal can be combined with the cancellation signal from the cancellation path using a power combiner 920 (a simple resistive combiner or even a microstripline directional coupler can provide a lower cost option). In many embodiments, the FINDER design is self-calibrated for each frequency, so changes in match or gain on either the cancellation signal or received signal are essentially compensated by the closed loop cancellation process. Field and laboratory testing have shown that a Low Noise Amplifier ("LNA") may not be needed before the combiner and could be problematic because of the very strong signal coupled from the transmit antenna. A transmit/receive isolation of −20 dB is typically expected, so a radiated +10 dBm signal would appear at the receiver input at −10 dBm. With such a strong signal, front end gain is not typically needed. In many embodiments, a small ceramic bandpass filter combined with amplifier 921 with a nominal range around 2.8 to 3.4 GHz can be used before sending the signal to the demodulator 922. Although extending below lowest transmit frequency of 3.1 GHz, the filter can reduce potentially troublesome interference in the 2.45 GHz ISM band, which is used for everything from microwave ovens to WiFi links.

After most of the static clutter contributions to the received signal are removed, the remaining signal can then be amplified via a chain of bandpass filters and monolithic amplifiers. The bandpass filters can be identical to the one used at the input, inserted between each amplifier to reduce the chance of oscillation at an out of band frequency. The monolithic amplifiers (as represented in combination as 921 in FIG. 9) in many embodiments are typical of MMIC devices with a bandwidth of DC to 8 GHz. The interstage filters reduce the possibility of there being spurious oscillations resulting from unwanted signals coupling from output to input at just the wrong phase.

In many embodiments, a power divider sends the signal to an I/Q demodulator and to a test port. The test port can be used to measure the total power or view the signal spectrum on a spectrum analyzer. Such an RF power measurement monitor port might be useful in system self-calibration and in initial adjustment of the cancellation signal, particularly if the signal is strong enough to saturate the I/Q demodulator. However, any anomalies in the receive chain can be determined by looking at the output of the I/Q demodulator as the cancellation path is adjusted over the range of values. A 90 degree change in the cancellation path should show up as a comparable change in the output of the quadrature demodulator. As a result, several embodiments of the receiver module 904 do not include a monitor port.

Typically, monolithic amplifiers are stable with almost any load. Further, at the low powers that are utilized, the power reflected from the antenna doesn't cause many problems with dissipation in the amplifier. Furthermore, leakage within the RF module from the transmit to receive side (e.g. Tx reflected power from the antenna mismatch coupling back through power dividers, etc.) is generally small, and essentially unchanging over time scales of minutes. In fact, the leakage looks like static returns from clutter, which can be cancelled by fundamental operations as discussed above.

Figure 10:
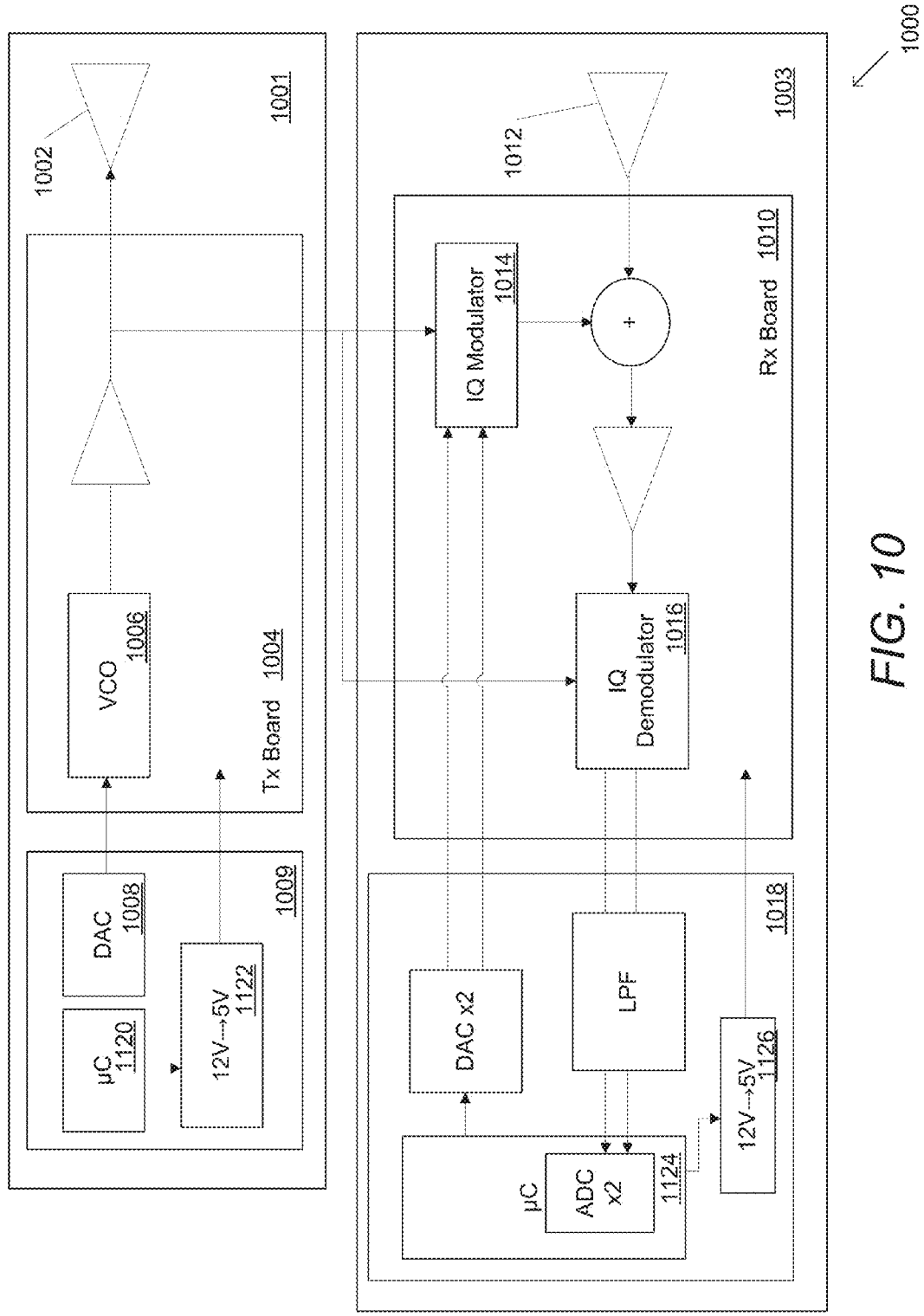
FIG. 10 is a block diagram illustrating separate transmit and receiver RF modules with digital interfaces in accordance with an embodiment of the invention

Although a combined RF module with a transmitter section and a receiver section are discussed above with respect to FIG. 9, an RF module can be separated into transmitter and receiver modules where each RF module is connected to its own digital interface. A system comprising transmitter and receiver modules in accordance with an embodiment of the invention is illustrated in FIG. 10. The system 1000 can include a transmitter module 1001 having a transmitter antenna 1002 that is connected to a transmitter board 1004. The transmitter board 1004 can include a VCO 1006 driven by a DAC 1008 that is part of the digital interface 1009. In various embodiments, the digital interface 1009 is connected to an embedded computer as described above. The system 1000 can also include a receiver module 1003 that includes a receiver board 1010 that is connected to a receive antenna 1012. The receiver board 1010 can include I/Q modulators 1014 and demodulators 1016 (and various buffers and amplifiers) for cancellation path processing as discussed above. In various embodiments, the receiver board 1010 is also connected to a digital interface 1018 that connects to an embedded computer or host computer for signal processing. In many embodiments, the microcontroller 1120 can control power to the transmitter board 1004 using a controllable DC/DC converter 1122. Likewise, a microcontroller 1124, part of the digital interface 1018 can control and supply power to the receiver board 1010 using a controllable DC/DC converter 1126. In a number of embodiments, a single board RF Module with a transmitter, cancellation path, and receiver all on one printed circuit board ("PCB") can be utilized.

Although specific RF modules are discussed above with respect to FIGS. 9-10, any of a variety of RF modules as appropriate to the requirements of a specific application can be utilized in accordance with embodiments of the invention. Digital Modules for use in FINDER systems in accordance with embodiments of the invention are further discussed below.

Digital Modules

FINDER systems can include one or more digital modules that contain data converters such as (but not limited to) analog-to-digital converters ("ADCs") and DACs serving as the interface between RF modules and the signal processing software. In various embodiments, the digital modules can be part of the RF module as discussed above with respect to FIG. 10 (see digital interface 1009 and 1018). Typically, a microcontroller or FPGA can read ADCs at a rate of 100-200 kilosamples per second. In many embodiments, sampled data can be filtered and decimated (reduction in sampling rate) to a few hundred samples/second for target detection. The digital module also provides a high level interface to the DACs that control the VCO frequency and the I/Q control voltages for the cancellation path.

Although an off the shelf data acquisition system can be used, the digital module can be implemented with monolithic integrated circuit ADCs similar to those used in digital audio systems. The ADC may be either integrated with the microcontroller or a separate device, depending on the overall system design. One factor to consider can be the number of beams and frequencies used to achieve the desired performance, which in turn affects whether multichannel data converters should be used.

In various embodiments, a testing unit can be an off the shelf National Instruments Compact RIO unit with ADC, DAC, and digital plugins. In various embodiments, this can be replaced by a single card with data converters and the necessary digital processing for filtering. The interface between the digital module and the embedded computer can includes a variety of data transfer standards including (but not limited to) Universal Serial Bus ("USB") or Ethernet. Typically, the ADC has sufficient conversion speed to allow sampling the output of the I/Q demodulator signals. There is a tradeoff with conversion speed—fast conversions relax the requirements on the low pass filters at the I/Q outputs, while consuming more power and introducing more digital noise. Slower conversions can involve lower cutoff frequencies on the low pass filter with the added advantage of lower power consumption. However, the lower cutoff frequency of the analog filters ahead of the ADC can increase the amount of time it takes for the values to stabilize. A fast conversion typical utilizes digital processing to filter and decimate to a reasonable rate for the heartbeat detection and victim detection processes.

The basic sample rate for victim detection can be 300-500 Hz, which is more than 100 times faster than the heart rate which is about 0.5 to 2 Hz (usually given as 30-120 beats per minute). This sample rate is sufficiently high for adequate resolution of the fine structure and morphology of the heartbeat (and respiration) signals. In many embodiments, a decimated sample rate of 200 Hz can be selected. This rate is sufficiently higher than the heart and breathing rates, and their harmonics. As previously discussed, the FINDER system typically operates between frequencies and/or beams and revisits the same beam/frequency combination at a 500 Hz rate. With 16-32 beam/frequency combinations, there is approximately 62.5 microseconds per beam/frequency implying that the ADC measurement can be made in around 50 microseconds. This allows for 10 microseconds for the microwave oscillator and cancellation paths to settle. Thus, analog filters on the I/Q output should have a time delay/settling time on the order of 10-20 microseconds, or around 50-100 kHz cutoff.

The I/Q control for the cancellation path can have more stringent requirements than the VCO tuning. The settling time can be chosen as one microsecond for the same reasons as the VCO tuning DAC. The DAC should have enough bits that it does not limit the accuracy with which the DC I/Q voltages are set, rather the performance should be limited by the modulator and other components. The modulator performance specification typically is called out as a Carrier Suppression/Nulling, and for the device selected for specific embodiments, it is −40 dB. This specification provides some guidance, but it is not directly usable since it defines the performance where I/Q are driven by sine waves with the DC offset adjusted to minimize the carrier signal. This performance implies that the DC bias can be set to 1 part in 100 (40 dB in power is a factor of 100 in voltage), or about 7-8 bits equivalent resolution. In FINDER applications where the I/Q inputs are DC voltages substantially better performance is typical. Laboratory measurements of specific modulators using a precision power supply have shown that 10 mV steps out of 60V (corresponding to about 0.3 mV out of a 2 V swing), or 1 part in 6000 can be easily resolved using a vector network analyzer to measure the phase and amplitude. This corresponds to around 13 bits of resolution. Therefore a DAC with 14 or 16 bit performance can be utilized. Typically, a perfect null is not required and with appropriate gain distribution signals can be seen in less than ideal conditions.

The DAC should have enough bits to step in small enough frequency intervals to support some level of range processing using stepped frequency CW. In general, this suggests that the phase difference of the microwave signal at the maximum range should vary less than 180 degrees between two successive steps. For a maximum range of 30 meters, a round trip distance 60 meters, this is 5 MHz. For a typical monolithic VCO tuning voltage range of 0 to 5V tuning over the entire 300 MHz range, this means at least 60 steps or a 6 bit DAC should be chosen.

In many embodiments, the DAC should settle fast enough that FINDER can step between frequencies or beams and have enough time for the I/Q demodulator measurements to settle, before moving to the next combination. The VCO modulation bandwidth for typical VCOs is >50 MHz (implying response times of 20 ns or faster), so the DAC response and settling can be the limiting factor. In various embodiments, low pass filtering can be applied in the analog tuning voltage chain to avoid unwanted noise modulation, thus, a notional low pass of 100-200 kHz can be selected, and the DAC should convert in less than a microsecond.

Although specific digital modules are discussed above, any of a variety of digital modules as appropriate to the requirements of a specific application can be utilized in accordance with embodiments of the invention. Sensor modules that integrate digital and RF modules for target detection in accordance with embodiments of the invention are further discussed below.

Integrated Sensor Modules

Figure 11:
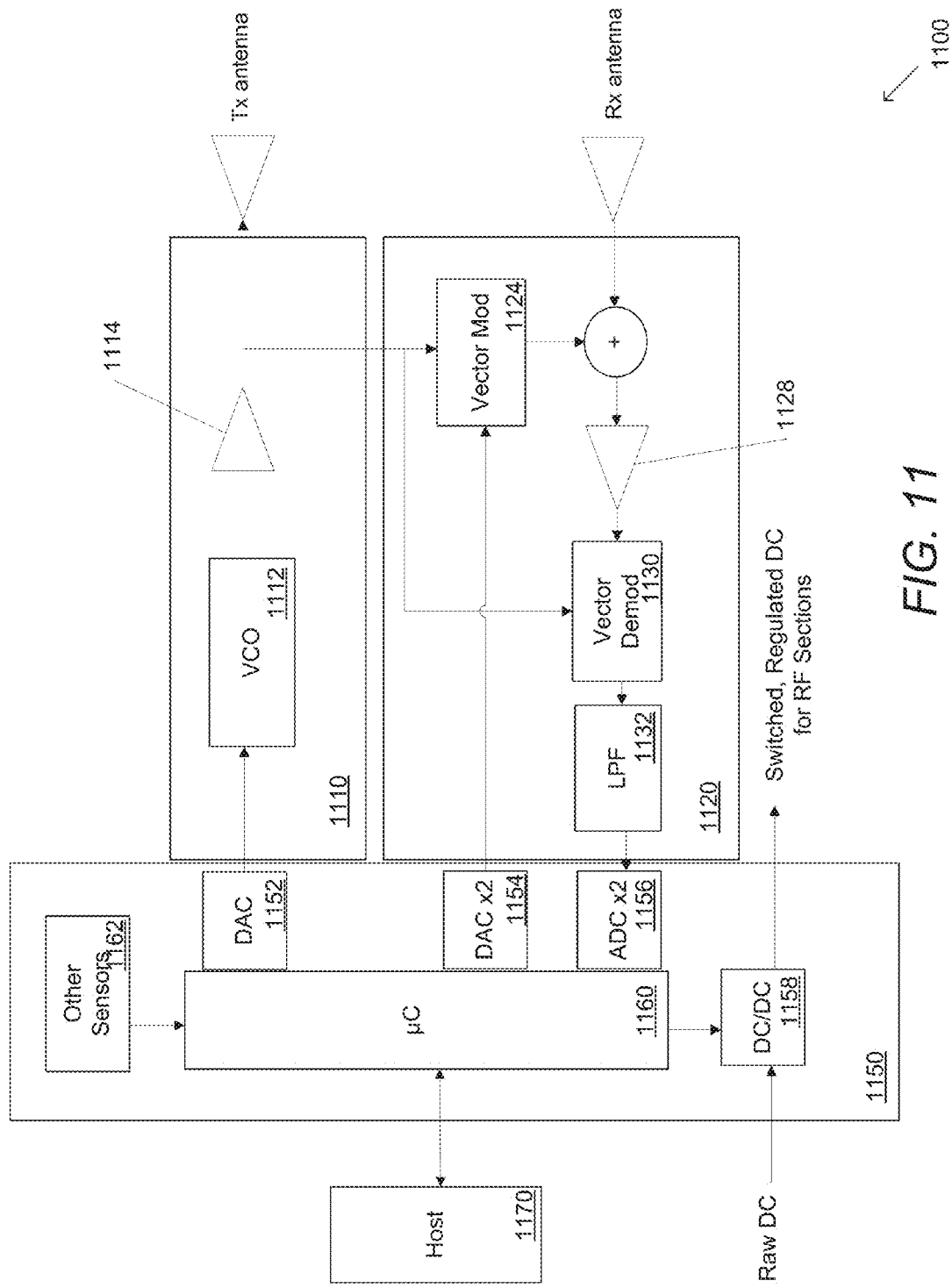
FIG. 11 is a block diagram illustrating a sensor module comprising a microcontroller unit integrated with transmitter and receiver units in accordance with an embodiment of the invention.

Various functionalities (and components) of RF and digital modules can be integrated into sensor modules for target detection and biometric measurement. An integrated sensor module in accordance with an embodiment of the invention is shown in FIG. 11. The sensor module 1100 can include a transmitter unit 1110, a receiver unit 1120, and a microcontroller unit 1150, where the microcontroller unit can be configured to calibrate and initialize various parameters including (but not limited to) the transmit frequencies and cancellation paths as further discussed below. In many embodiments, the microcontroller unit can include a microcontroller 1160 connected to various data converters 1152, 1154, 1156, and 1158 for communication with the transmitter 1110 and receiver 1120 units. Further, the microcontroller unit can utilize various data converters in processing from frequency steps to range as discussed above. In addition, the microcontroller can be connected to a host computer 1170 and various other sensors 1162.

In several embodiments, the transmitter unit 1110 includes a VCO 1112 and various amplifier stages 1114 to generate an appropriate transmit signal. In generating a transmit signal, the VCO can receive input from the microcontroller 1160 via the DAC 1152 using at least one frequency control signal. Further, since the output frequency can vary strongly with temperature, the microcontroller can utilize a temperature sensor 1162 (with a lookup table or other techniques) to determine appropriate tuning voltages to send to the VCO. As a note, to improve frequency stability, the microwave source may use a phased locked loop (PLL), where the frequency changes can be accomplished by the microcontroller setting programmable registers in the PLL frequency divider. Further, depending on the requirements of a specific application, the microcontroller unit can periodically change the transmitter frequency according to a predetermined pattern so that the module may be used a stepped frequency radar for increased range resolution, to mitigate the effect of interference (by avoiding interfering signals), and to mitigate the effect of the radar's RF emissions on other RF systems (e.g. for regulatory compliance).

In various embodiments, the receiver unit 1120 can include a chain of amplifiers to increase the level of a received signal, a vector modulator 1124 that utilizes a sample of the transmitted signal as reference, and a cancellation path that can be configured to adjust the amplitude and phase of a sample of the transmitted signal and combine it with the received signal before amplification. In several embodiments, the vector modulator can receive input from the microcontroller 1160 via a at least one DAC 1154 (typically 2 DACs are utilized) using at least one cancellation path control signal. Typically, the received signal, after cancellation of the transmitted signal, is amplified in a chain of amplifiers 1128 before being coherently demodulated by a vector demodulator 1130. In many embodiments, the RF amplifier chain and the post detection buffer amplifier gains are normally chosen so that the thermal noise of the first amplifier is more than the minimum signal for the ADCs, while preserving the maximum dynamic range. In practice, variable gain in the receiver has not been found to be needed, but adding it to the design can be straightforward, and may allow the use of lower resolution ADCs. Since the sensor module can be used for detection of relatively low frequency phenomenon over a time span of seconds, the gain control can be slow, stepped, and nonlinear, saving complexity and cost.

In various embodiments, the vector demodulator 1130 produces two baseband signals for the inphase and quadrature components (I and Q) and uses a sample of the transmitted signal as the reference or local oscillator, thus performing a classic homodyne detection. The I and Q outputs can be filtered using a low pass filter ("LPF") 1132 and buffered before being fed to at least one ADC 1156 (typically a two ADCs are utilized). As with the vector modulator, the FINDER implementation typically utilizes a monolithic integrated circuit to perform this function, however, alternate implementations are possible, such as entirely passive system using quadrature hybrids, mixers, and power dividers as further discussed below. It is expected that without any cancellation signal (e.g. the vector modulator set to maximum attenuation) the ordinary reflected signal received by the receiver will saturate the amplifiers and ADC and thus the cancellation signal must be properly adjusted. Similarly, the demodulator function typically operates on a very narrow band signal, and errors in phase, gain, or offset can be compensated in the signal processing downstream. In many embodiments, the microcontroller unit can be configured to execute calibration processes to adjust the amplitude and phase of the cancellation signal to optimize the dynamic range. In various embodiments, the temperature measurement can provide an a priori starting point for adjustment of the I/Q cancellation path. Thus, knowing the temperature can speed up the calibration process by providing a closer first estimate.

Further, the microcontroller unit can perform a number of additional functions which may be needed in a practical system. For example, the DC power to the RF circuitry can be cut when not taking measurements, or the microcontroller can be configured to perform a repetitive sequence of turning on the power, waiting for the components to stabilize, making a measurement, storing or transmitting the data, and then shutting down. Further, the microcontroller 1160 can measure the unregulated supply voltage and report it to a host computer 1170 for diagnostic purposes (e.g. estimating the state of charge of a battery power source or validating that DC power is available at all). Furthermore, the microcontroller may control other parts such as (but not limited to) colored LEDs that can be illuminated in different colors depending on the operational mode, or for diagnostic purposes.

As discussed above, the microcontroller unit can include other sensors 1162 such as an accelerometer or rate sensor for applications involving movement, where the microcontroller can utilizes such data to either to warn the user that movement occurred or to help compensate for the effects of the motion on the radar signals. Further, the microcontroller unit can include a DC to DC converter 1158 to convert unregulated DC supply voltage from a battery (9-18 volts in some embodiments) to a regulated 5 voltage (5 volts) for use by the RF circuitry.

In many embodiments, the microcontroller 1160 can communicate with the host computer 1170 or other device using a variety of interfaces implemented in manners well known to one of ordinary skill in the art. For example, in the implementation for FINDER, a USB slave interface provides a virtual serial communications port using industry standard protocols. The USB interface also provides a means by which new software may be loaded and stored in the microcontroller. In many embodiments, the sensor module can also provide a conventional serial port interface, which may be configured for various signaling (baud) rates and character formats. The serial port may also be configured for other serial interfaces such as I2C or SPI. Finally, the module can provide an external synchronization interface to allow multiple modules to be interconnected and sample simultaneously so that a single target can be detected by multiple sensors.

Figure 12A:
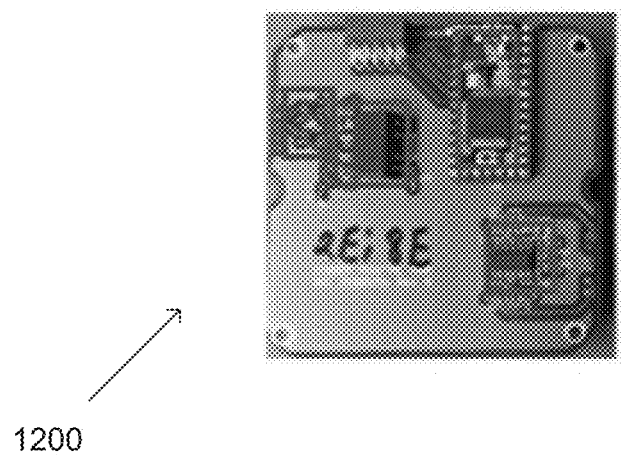
FIGS. 12A-C illustrate implementation of a sensor module using three printed circuit boards (PCBs) in accordance with an embodiment of the invention.
Figure 12B:
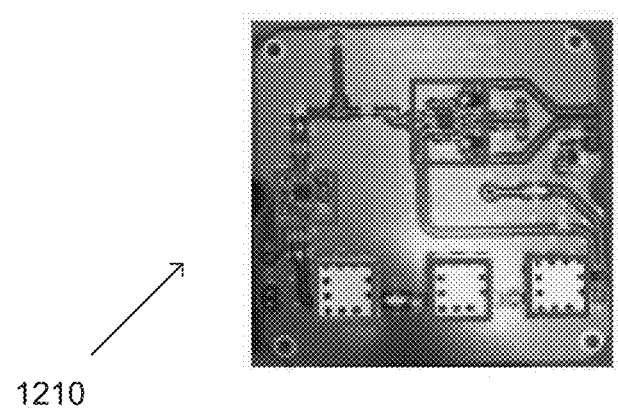
Figure 12C:
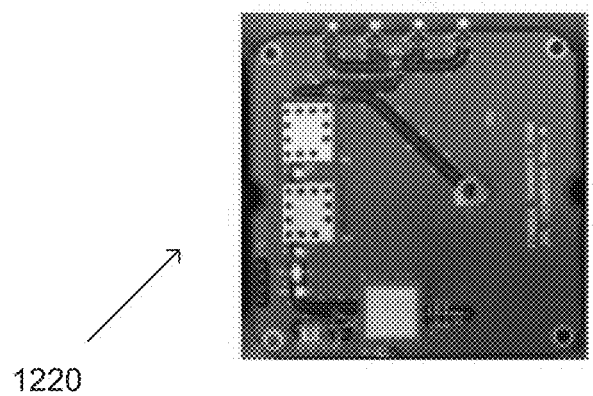

A sensor module implemented using three PCBs in accordance with an embodiment of the invention are shown in FIGS. 12A-C. The PCB 1200 can include digital components such as (but not limited to) the microcontroller unit as described above. In several embodiments, a separate PCB 1210 can include the receiver unit as described above. In various embodiments, an additional PCB 1220 can include the transmitter unit as described above. In many embodiments, the 3 PCBS 1200, 1210, and 1220 can be integrated into a single 3"×3" aluminum housing which can serve as a ground plane for a linear polarized air dielectric patch antenna.

Although the sensor module is described above as separate microcontroller, transmitter, and receiver units, various configurations of the module are possible. For example, the transmitter and receiver units may be combined in a single package in the simplest configuration. In more complex configurations, modules may include only the transmitter unit or only the receiver unit, with the reference signal carried between modules by coaxial cables or implemented in a manner well known to one of ordinary skill in the art. In the context of the FINDER life detecting radar, five separate RF modules can be used where one module includes a transmitter board, and four modules include four receiver boards, respectively, where each board can be further connected to separate antennas, each facing in a different direction. In various embodiments, a steerable beam antenna may be created by using multiple transmit or receive antennas in an array configuration. In a further configuration an external antenna, perhaps of high gain for narrow beam width, or part of a probe for crevices or hostile environments may be utilized.

Although specific sensor modules that integrate microcontroller units with transmitter and receiver units are described above with respect to FIGS. 11-12C, any of a variety of sensor modules utilizing microcontroller, transmitter, and receiver units as appropriate to the requirements of a specific application can be utilized in accordance with embodiments of the invention. Alternative discrete implementations in accordance with embodiments of the invention are discussed further below.

Alternative Discrete Implementations

As discussed above, a sample of the transmitted signal can be passed through a vector modulator to adjust the amplitude and phase. The output of the vector modulator can then be attenuated so that the maximum signal is approximately equal to the power normally received by the antenna (approximately 20 dB down from the transmit power—this allows the maximum range for adjustment of the cancellation signal). Typically, the fixed attenuation should be tailored to the specific implementation with the following guidelines:

the maximum level of the cancellation signal should be large enough to completely cancel the received signal, when the coupling from transmit antenna to receive antenna is maximum. In the typical radar implementation (as in FINDER) the majority of the coupling is due to the packaging of the modules within the outside enclosure, but in other instances (e.g. when the modules are used directly in contact with some solid object), the reflection from the object might be stronger;

the maximum level of the cancellation signal should not be too large, because there is limited resolution in the phase and amplitude adjustment (vector modulator) and too large a signal, combined with large adjustment steps, may make it impossible to achieve effective cancellation; and the maximum level should be small enough that when there is no receive signal (e.g. if the antenna is replaced by a termination, or left unconnected), that the receiver chain is not damaged.

Figure 13:
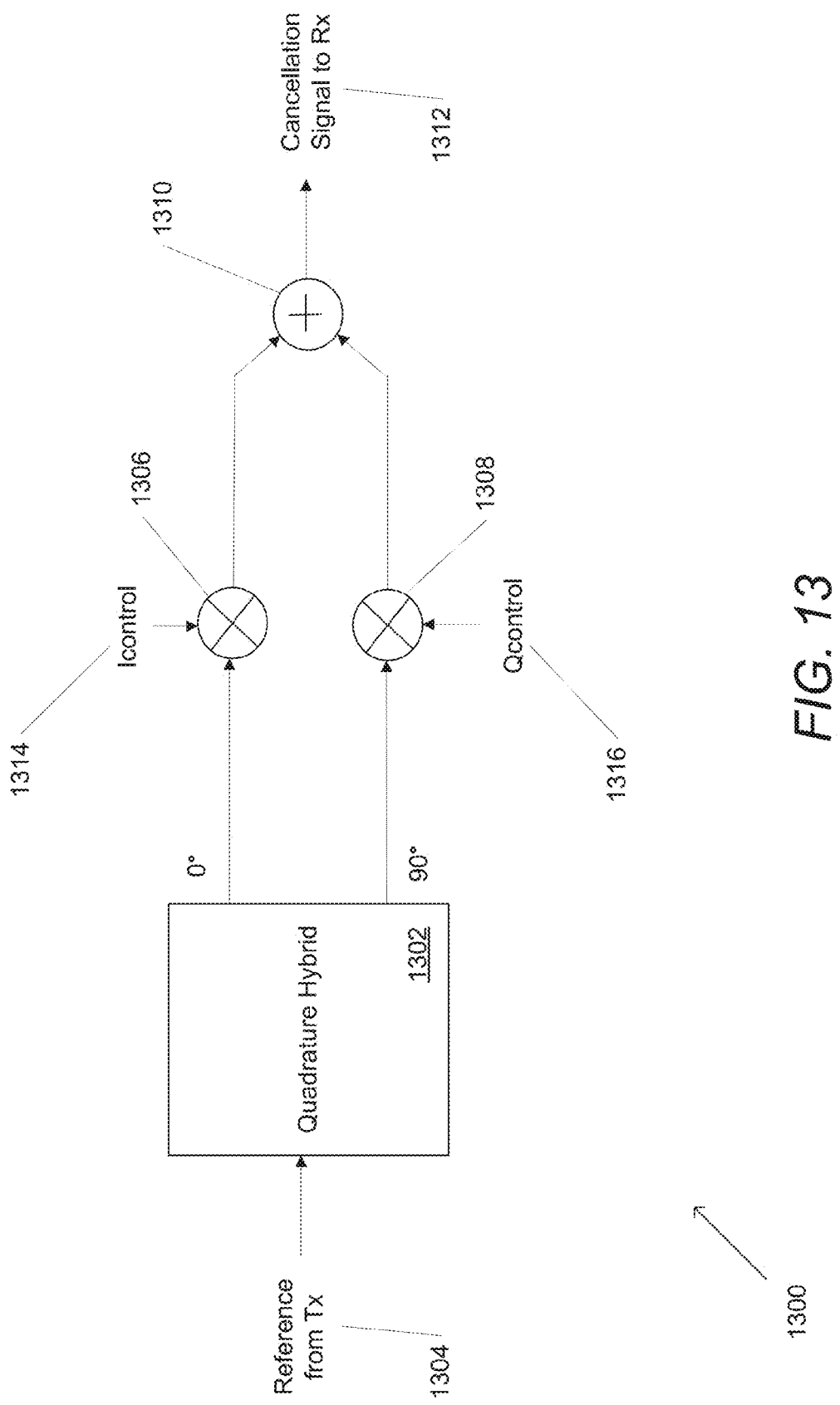
FIG. 13 a block diagram illustrating a discrete implementation of a vector modulator in accordance with an embodiment of the invention.

While the FINDER implementation uses a monolithic vector modulator integrated circuit, other lower power implementations could use a quadrature hybrid, discrete mixers, and a power combiner. An alternate discrete implementation of the vector modulator for the signal cancellation path is shown in FIG. 13. The discrete implementation 1300 includes a quadrature hybrid combiner 1302 configured to sample the transmitter signal as a reference 1304. In many embodiments, the sample signal is transmitted from the quadrature hybrid to discrete mixers 1306, 1308 where the respective signals are combined using a power combiner 1310 to generate a cancellation signal 1312 that is sent to the receiver unit. A control signal 1314 controls the amplitude of the signal coming out of mixer 1306, and a control signal 1316 controls the amplitude of the signal coming out of mixer 1308. Since the phase and amplitude adjustment is typically done empirically (by a calibration processes executing on the microcontroller or elsewhere) for best cancellation, there may not be a need for the vector modulator to have good amplitude or phase balance, be linear, or have uniform performance over the operating frequency band. It may only be necessary that the two or more adjustment signals can produce a cancellation signal that spans all the possible received signal phases and amplitudes. Furthermore, since in most implementations, the reference signal has a much larger amplitude (e.g. 20 dB in the FINDER implementation) than the needed maximum cancellation signal, the implementation may have significant loss, unlike the usual case in communications equipment. This allows the use of under driven mixers, discrete diode attenuators, and transmission lines of various lengths, all of which are often not used because their control characteristics are non-linear, they are not constant across the band, or they have a lot of loss.

Although specific alternative discrete implementation of a vector modulator for use in signal cancellation paths are discussed above with respect to FIG. 13, any of a variety of alternative discrete implementations of vector modulators for generating signal cancellation paths as appropriate to the requirements of a specific application can be utilized in accordance with embodiments of the invention. Design considerations for integrated sensor modules in accordance with embodiments of the invention are discussed further below.

Sensor Module Design Considerations

Although a microcontroller unit can be programmed and provide automated controls, the selection of components, gains, and data converter resolution may depend on design tradeoffs. For example, at higher transmitted powers, the overall Signal to Noise Ratio can improve but it also raises the power dissipation and may raise regulatory concerns for power spectral density and/or RF exposure safety. In many embodiments, FINDER utilizes a transmitted power between 1 and 10 milliwatts. It is noted that the stability of transmitter power over temperature and life is typically not important, as it affects mostly the overall system sensitivity, not the detection performance.

Another design consideration includes selecting the resolution of the DACs driving the cancellation path modulator where higher resolution can mean that the residual signal in the receiver will be smaller (e.g. the cancellation is better) thereby improving the overall system dynamic range. However, higher resolution DACs typically consume more power and are more costly. In several embodiments, FINDER uses a 12 bit DAC controlled via SPI serial interface.

The noise figure of the receiver amplifier can be another design consideration. Typically, the noise figure of the receiver amplifiers affects the overall signal to noise ratio, and ultimately the sensitivity of the system. Practical experience has shown, though, that it is easier to increase the output of the transmitter by a few dB, than to drive the noise figure of the receiver lower. In addition, the noise characteristics of the analog low pass filters following the vector demodulator can be more important than the RF noise, since at very low frequencies (1 Hz), the 1/f (flicker) noise is larger than thermal white noise. Thus, selecting appropriate low noise operational amplifiers may be important design consideration.

Finally, the higher the resolution of the ADCs that digitize the output of the vector demodulator, the more of the static, unchanging baseline can be cancelled in subsequent digital signal processing, and the performance of the cancellation path can be worse. However, increasing the number of bits in the ADC increases power dissipation, costs, and longer word lengths also increases the computational workload in the downstream processing. Increasing ADC resolution can also place requirements on the RF chain for more dynamic range (headroom for maximum signals, noise for the bottom). In various embodiments, the FINDER implementation utilizes a 16 bit ADC integrated with the microcontroller, although circuit noise and other factors can result in an ADC performance (Effective Number of Bits—ENOB) in the order of 13-14 bits.

The microcontroller can be configured to digitize the baseband I/Q signals at a sufficiently high rate that high frequency components passing through the low pass filter do not alias into the detection bandwidth. In many embodiments, a design tradeoff can exist between the sample rate and the low pass filter bandwidth, particularly if stepped frequency operation is desired. The low pass filter cutoff should be high enough that the delay through the filter is short compared to the dwell time at each frequency. A high cutoff frequency typically calls for a higher sampling rate for the microcontroller, which consumes processor resources and increases the power dissipation. In many embodiments of the FINDER radar, the I and Q samples are 16 bits at 50 kHz, and the analog low pass filters are cutoff at 10 kHz. Other frequencies may be more useful depending on the eventual application. For example, the sample rate may be chosen to avoid interference to or susceptibility from other systems. A system that does not need to rapidly change frequencies may benefit from using analog low pass filters with a lower cutoff and a lower sample rate, which will likely greatly reduce the power consumption.

In several embodiments, the digitized signal is then low pass filtered and decimated to a rate that is appropriate for the signals being sensed. For heartbeats, a rate of 200 Hz has been found to be a good compromise between being able to resolve fine details of the heart signal and computational burden on the feature extraction process. In various embodiments, the microcontroller then sends the digitized and filtered data samples to a host computer (or stores them locally for later use). In the FINDER implementation, the decimation is done in three steps with the first two using Cascaded Integrator Comb filters, and the final step a FIR filter with characteristics chosen to reject the radar signals from fluorescent and gas discharge lighting. At this point, the FINDER module output data stream is 200 Hz I/Q samples of 18 bit numbers, that is, about 7200 bits/second.

In many embodiments, once decimated to a suitable low rate, further processing may be done in the microcontroller to further reduce the data rate. For example, in FINDER, the eventual processing is done on two bandpass filtered signals for respiration and heart rate, each at a sample rate of 20 Hz, so a 1 kbit/second data rate can be reasonable. This would facilitate the use of the sensor in long duration monitoring applications, where the data is logged to non-volatile memory within the sensor (e.g. Flash memory in the microcontroller or a removable media such as a SD card).

Figure 14A:
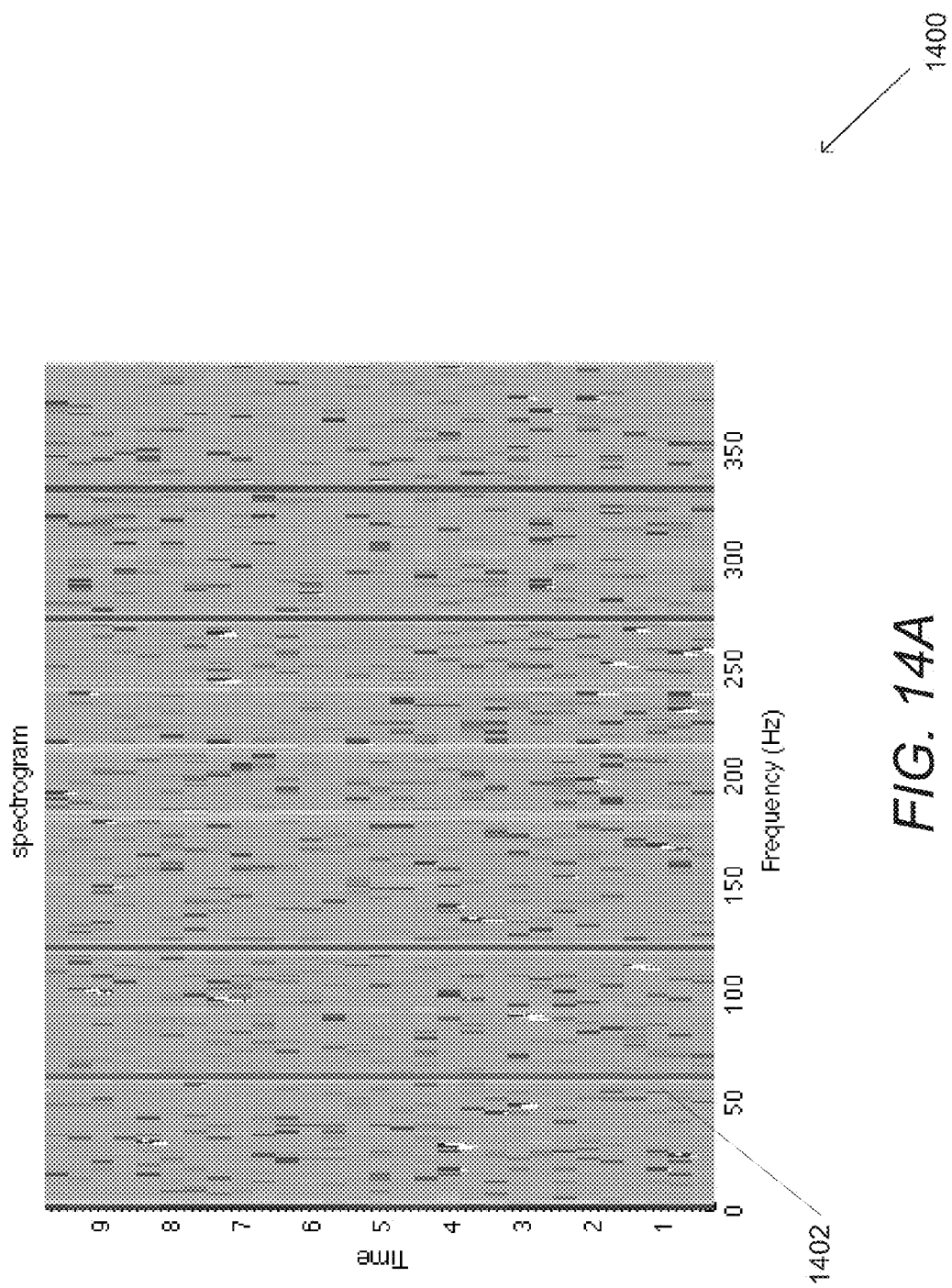
Figure 15:
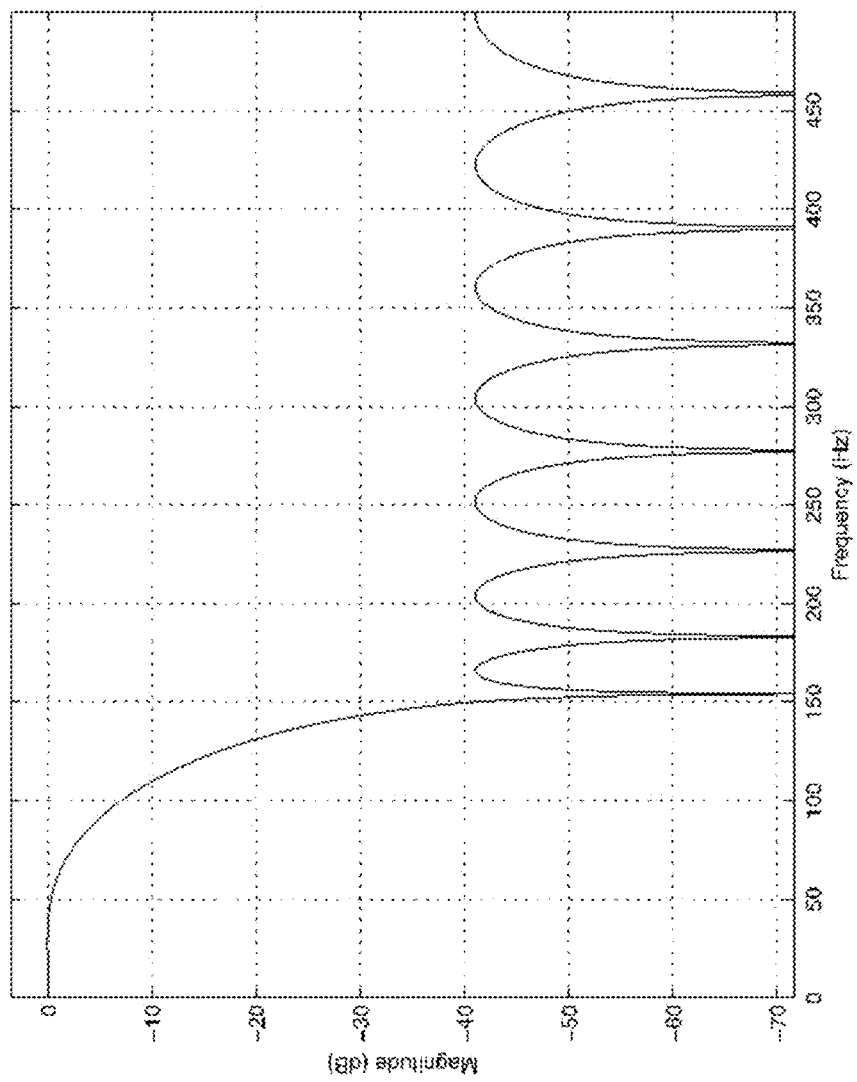
FIG. 15 is a graph illustrating a finite impulse response ("FIR") filter characteristic in accordance with an embodiment of the invention.

Further, when the sensor module is used in areas with fluorescent or other gas discharge lighting, there can be strong components in the received signal at the power line frequency and its harmonics (e.g. 60 Hz, 120, 180, etc. in the United States). Spectrograms illustrating data collected using a sensor module in fluorescent lights in accordance with an embodiment of the invention is shown in FIGS. 14A-B. The chart 1400 shows the spectrogram of 10 seconds of sample data, where strong harmonics 1402 can be visually noticed as narrow bands at various frequencies. The power spectrum plot 1450 illustrates the strong harmonics 1452 as spikes at various frequencies (Hz). The digital filter design and sampling rates should be carefully chosen to ensure that the significant energy in these harmonics does not alias into an area of interest for heartbeat detection (e.g. around 1 Hz). Although a comb or notch filter may be used to remove these frequencies, however, in field deployed applications, the frequency control from temporary power generators may not be sufficiently tight that a single filter would work; and, there is also the possibility that there is a mix of 50 Hz and 60 Hz power. Further, a graph illustrating a sample finite impulse response filter characteristics in accordance with an embodiment of the invention is illustrated in FIG. 15. Although data illustrating sensor characteristics are discussed above with respect to FIGS. 14A-15, any of a variety of data illustrating sensor characteristics as appropriate to the requirements of a specific application can be utilized in accordance with embodiments of the invention. Processes for sensor module calibration and setup in accordance with embodiments of the invention are discussed further below.

Sensor Module Calibration and Setup Processes

The microcontroller can implement several self-calibration and self-check functions to facilitate the automated adjustment of the cancellation path for enhanced module performance as further described below. In many embodiments, the microcontroller can be configured (using various software) to perform automated adjustment of the cancellation path in two steps. In the first step, it can systematically vary the control signals to the vector modulator to completely cover the adjustment range. In the FINDER implementation, a uniform grid of I and Q values that is 13×13 can be utilized, stepping the 12 bit DACs in steps of 300 from 300 to 3900 (out of a range of 0:4096). For the majority of the grid steps, the cancellation signal actually makes things worse (it is too large to cancel the small signal being cancelled), causing the signal to the ADC to be out of range. For the relatively few grid steps where the signals are within range, typically 3-10 grid points out of 169 examined, the best of them can be selected. If none of the points is within range or the region in the grid where they are located is on the edge of the range, an error can be declared and calibration stops, since this is indicative of some fundamental problem with the module (the most common cause is that no transmit signal is being generated). In various embodiments, the grid steps must be fine enough that there is a good chance that at least 1 grid step will produce enough cancellation for the signal to be in range.

This process can be repeated for each operating frequency, and can be dramatically shortened by starting with those grid points near where the expected operating point is (determined from previous experience, and the temperature of the module), and then spiraling out until all grid points are out of range. The I/Q measurements at each grid point should use enough samples to insure that a transient doesn't have a large effect on the measurement. The sample duration should also be selected so that a large periodic interfering signal (e.g. the radar reflection from fluorescent lights) does not provide a spurious value. For example, if the I/Q integration were done for 8 milliseconds, this would accumulate about a half cycle of a 60 or 50 Hz interfering signal, and that would cause a bias in the integrated value.

Two approaches to this are to integrate for a time of multiple cycles or to integrate samples at random times, and integrate multiple samples for each grid point. That is, one could take 0.5 millisecond samples at each of the 169 points in the 13×13 grid, repeating it for 100 milliseconds, so that each of the 169 values essentially integrates for that time span (which is an integer multiple of both 50 and 60 Hz periods). The tradeoff is in how long to spend calibrating vs the ultimate performance. In practice, with FINDER it has been found that recalibrating once every hour or after a major power cycle is sufficient. A more dynamic approach is also possible in a multi-sensor system, where the acquired data can be monitored, and as the baseline of one or more of the sensors starts to drift away from zero, a recalibration can be performed. In a periodic logging application, where 30 seconds of data is collected every half hour, recalibrating just before each measurement may be appropriate.

Once the coarse grid calibration has determined an approximate setting for the cancellation, a fine search can be conducted by iteratively moving the cancellation to attempt to drive the I/Q outputs to zero (minimum signal). There are many possible approaches here, including grid searches, steepest descent, Fletcher-Powell, and others. In several embodiments, FINDER uses a stepwise search with a gradually reducing step size. Starting with the current location, a trial is made in each of four directions (increased/decreased I/Q) and as long as the new location is better, it becomes the new best estimate. When the 4 trials are greater, the step size is reduced by a factor of 2, and the process repeated, until the minimum step size is reached.

Typically, the results of both calibration steps should be verified before proceeding on to making a measurement. That is, after the grid search is complete, all the candidate grid steps should be re-measured, and if they vary significantly, the entire process should be repeated. This is because something may have occurred during the calibration process that caused an anomalous result such as (but not limited to) a strong interfering signal appeared, a battery failure, or the sensor positions were changed (e.g. the FINDER radar housing was moved during calibration). Likewise, after the fine search, the measurement can be repeated several times at the best estimate to insure that the value isn't changing very much from the original minimum. Processes for configuring a microcontroller unit in accordance with embodiments of the invention are discussed further below.

Configuring the Microcontroller Unit

In many embodiments, the microcontroller unit can utilize various microcontrollers including (but not limited to) the Teensy 3 (or 3.1) Development Board which is a 32 bit ARM-Cortex M4 platform that supports Arduino or programming directly in C language. Typically, a variety of software can be utilized on the Teensy 3 (or 3.1) microcontroller to send commands and receive responses as further described below.

Figure 16:
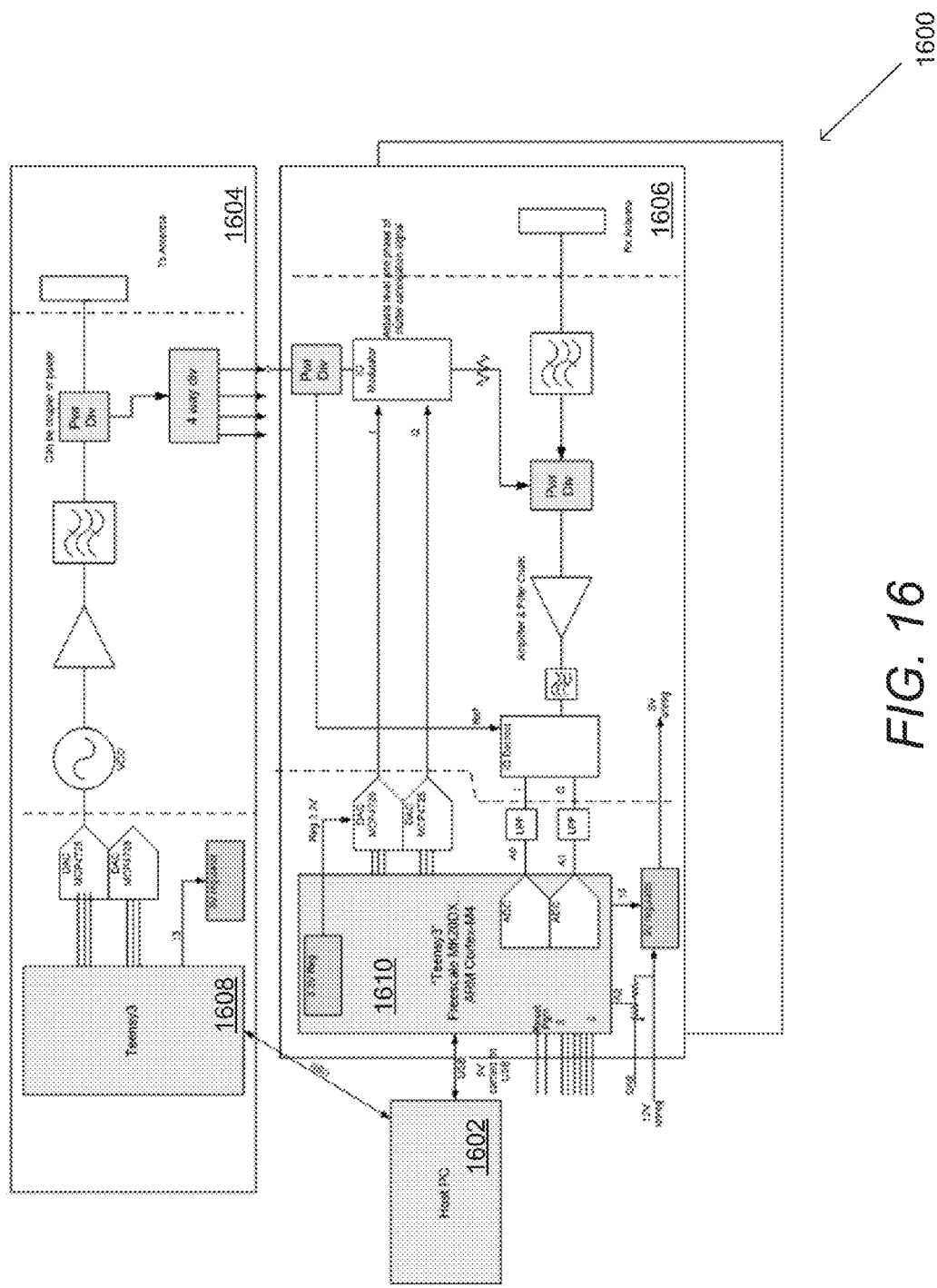
FIG. 16 is a schematic diagram illustrating a transmitter module and multiple receiver modules connected to a host PC in accordance with an embodiment of the invention.

A schematic diagram illustrating a transmitter module and multiple receiver modules connected to a host PC in accordance with an embodiment of the invention is shown in FIG. 16. Typically, a FINDER comprises 5 microwave sensor modules that includes 1 transmit module and 4 receive modules, all connected to a host PC running Windows. The sensor module 1600 can include an interface between the host PC 1602 and the transmitter unit 1604 and receiver unit 1606 such as (but not limited to) a serial port emulated by the USB interface. In many embodiments, the software executes on the Teensy3 (or Teensy 3.1) 1608, 1610 from PJRC[1], which is a Freescale ARM based microcontroller which supports the Arduino[2] software development process and peripherals. When power is applied to the host PC, power can be fed to a USB hub, which in turn can feed power to the Teensy3 microcontrollers in each module. The standard power on reset of the Teensyduino environment can be used to start the software. In other embodiments of the digital board, the power for Teensy is supplied by a regulator from the overall module power, rather than the USB, however this does not significantly change the functioning of the module or software.

[1] http://www.pjrc.com/store/teensy3.html
[2] http://arduino.cc/

Commands

As described above, the interface to the host PC emulates a serial port. Table 1 below describes the commands which can be sent to the microcontroller. The commands are case insensitive (that is, 'v' and 'V' are identical commands). Note that in some cases (when there's no argument), no terminating carriage return is needed. Typically, commands are processed one at a time and there is no queuing, other than that provided by the serial port. Further, there is no overlap between reading, parsing, and processing commands. In addition, while a command is being processed, the receive buffer is not being read.

TABLE 1

| Summary | Syntax | Details |
|---|---|---|
| Set I/Q value (Baseline) | B<I value><Q value><cr> | Sends I value to DAC 0 and Q value to DAC 1 |
| Set I | I<value><cr> | Also used to set tuning voltage for Tx |
| Set Q | Q<value><cr> | |
| Get last I/Q values set | L | Returns last two values set as ascii integers <I value> <Q value> |
| Read ADC I channel | 0 (digit 0) | Returns 16 bit value from A0 as ASCII integer |
| Read ADC Q channel | 1 (digit one) | Returns 16 bit value from A0 as ASCII integer |

TABLE 1-continued

| Summary | Syntax | Details |
|---|---|---|
| Read both channels and calculate magnitude | M | Returns sum of TBD samples (approximately TBD milliseconds) as I, Q, Magnitude |
| Coarse Calibrate | C | |
| Fine Calibrate/Tune | D | |
| Start Sampling | S <cr> S <number> <cr> | Starts taking I/Q samples decimated to 200 Hz. If a number is given, that many samples are collected and sampling stops Samples are currently returned as 2 ascii numbers per line separated by a space |
| End Sampling | X | Stop sampling, even if number has not been reached |
| Query Time | T | Returns microseconds since module powered on |
| RF power on | P | Turns on 5V power to RF circuitry |
| RF power off | O (letter o) | Turns off power |
| Retrieve version and Serial Number | ? | Returns module number, version number (integer) and MAC that is programmed in at factory MAC returned in nn:nn:nn:nn:nn:nn |
| Read temperature sensor | K | Returns raw ADC output and approximate converted temperature in C. |
| Read 12V bus voltage | V | Returns raw ADC output from voltage divider. Returns raw ADC value (0-65535) Approximate curve fit is V = 29.33/65536 * ADC − 0.04 |

Further, there are several commands which directly control the I/Q outputs that control either the vector modulator (for receiver modules) or the VCO frequency (for transmitter modules). In several embodiments, I and Q values are 12 bit integers in the range 0-4095, with 2048 being approximately midscale, subject to inevitable tolerances in the analog circuitry. The commands can cause the appropriate serial data string to be sent to the 12 bit DACs on the digital board. In addition, the I or Q values may be set directly with the corresponding I and Q commands. The B command may be used to set both at the same time. Note that the actual DACs are programmed sequentially, I DAC first. Furthermore, the L command retrieves the last values set to the DAC. This can be useful when getting the results of a calibration sequence, or to verify that the DACs have been set at all. Note that the DACs are NOT initialized to any particular value when the processor starts.

In various embodiments, there are 3 commands that provide low level access to the analog inputs. The 0 and 1 (digit 0 and digit 1) commands read the I and Q ADC respectively, and display the result. The ADC is read with the analogRead( ) function provided by the Arduino environment.

In a variety of embodiments, the magnitude command is used primarily to verify the correct setting of the I/Q baseband cancellation, and returns the averaged I and Q outputs of the demodulator, and calculates the magnitude. The command prints the scaled sum of 1800 measurements made at full processor speed. The scaling is such that the value is 10 times the average of the 16 bit ADC measurement, so the maximum is 327670 and the minimum is −327680. As a practical matter, the analog circuitry (low pass filters) ahead of the ADC mean that a value with absolute value greater than 250,000 is probably saturated. The magnitude is scaled so the max value is 2.00 (e.g. the I sum and Q sum are divided by 327680). However, it might be useful to change the scaling to give some more significant figures to allow better nulling. The 2 digits past the decimal point as current implemented only allows getting 20 dB down (e.g. 0.01 vs 0.00). The underlying routine uses readIQShort( ) which reads I/Q 1800 times and sums (after subtracting 32768 from the raw measurement), and then divides the sum by 180. So max+ is 327670, min negative is −327680. In many embodiments, this can take approximately 17 milliseconds (e.g. the sample rate is about 100 kHz), which is roughly one period of the line frequency. Since we may be seeing a target with strong 60/120 Hz, this can help minimize the effect. When operating in the 50 Hz range, 20 milliseconds would be appropriate. Other timing tests showed that the integer divide by 180 takes less than a microsecond, thus it may not be beneficial to by going to a power of 2 and shift right. Note, if the RF section is has not been powered on (P command), M will read close to zero.

Calibration and Initialization Processes

In many embodiments, the receiver unit cancellation path can be calibrated by using the C and D commands. The first command steps through the entire adjustment range of the path in fairly big steps to identify the approximate values of Iset and Qset that will null the clutter and coupling signals. The D command does a stepwise search with variable length steps to refine the Iset and Cset value to 2 LSB. Note that as the modules heat up, the calibration can change. In particular, as the transmitter unit warms up, the frequency changes, which changes the phase shift through the leakage and reference paths. Typically, if gain is 500-1000/LSB and max is 250k, then 500 LSB (out of 4000) saturates. The rotation of the adjustment box can be the phase shift between the cancellation path and the detector local oscillator, and should be fairly stable over life, and possibly over temperature. The size of the adjustment box is the gain of the cancellation path. In various embodiments, the adjustment box is about 10 times the size of the dynamic range of the detector.

In several embodiments, the calibration process does not yield useful results if the RF power is not on (P command), because the vector demodulator has no power, so the differential output is zero. The calibration process (C and D commands) is a process of finding the set of $I_{DAC}$ and $Q_{DAC}$ values that minimizes the vector sum of the cancellation signal (controlled by $I_{DAC}$ and $Q_{DAC}$) and the RF input signal (which is mostly the leakage between antennas and the reflections from nearby surroundings). The electrical properties of the system change with temperature and operating frequency, so the calibration process must be done before taking data.

Figure 17A:
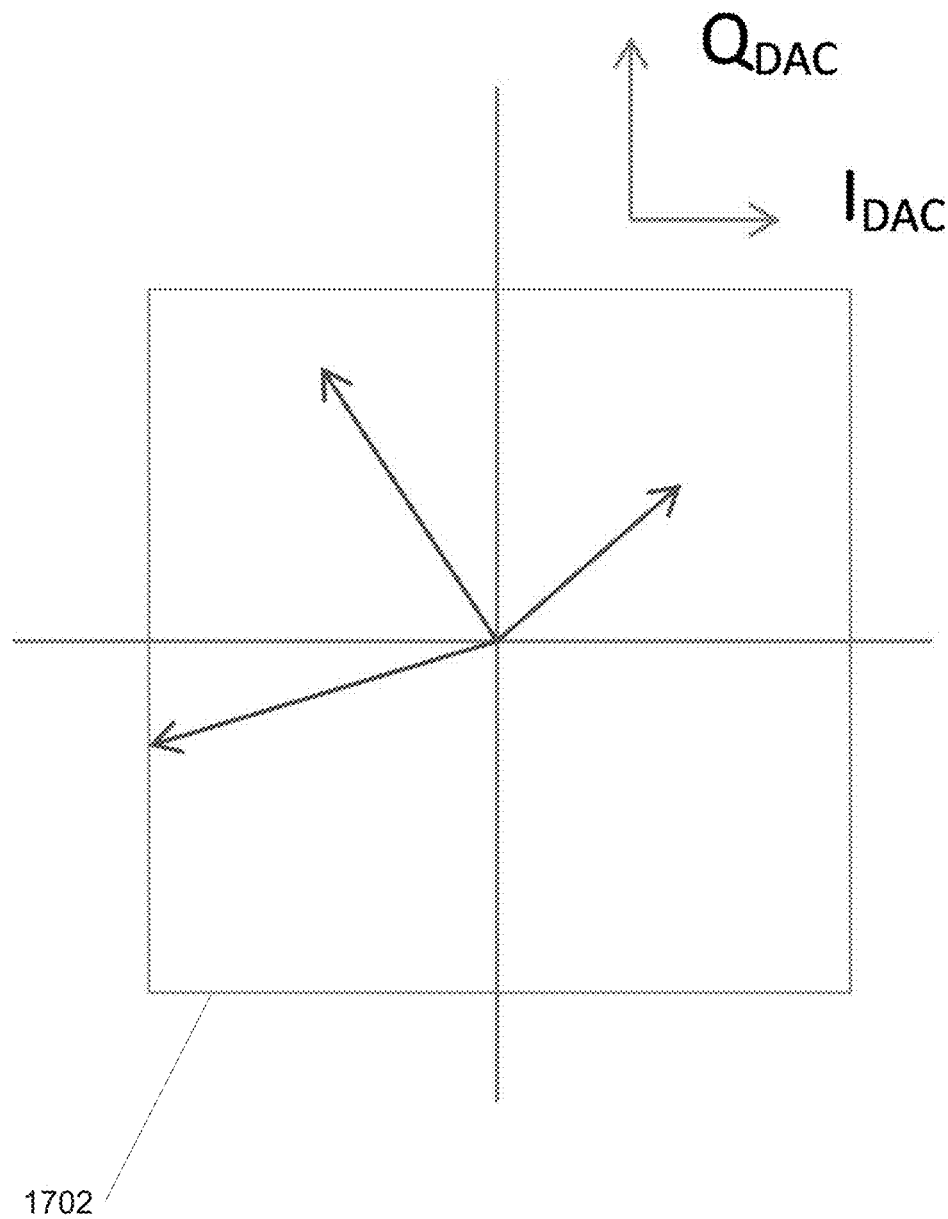
FIGS. 17A-C are graphs illustrating vector characteristics in accordance with an embodiment of the invention.

One way to visualize the cancellation and calibration process is to consider that the cancellation path can take on any value within a square box with ranges from −1 to +1 on each axis. A graph illustrating cancellation vectors defined by range of $I_{DAC}$ and $Q_{DAC}$ in accordance with an embodiment of the invention is shown in FIG. 17A. The graph 1700 includes a square box 1702 with ranges from −1 to +1 on each axis, where the x-axis is $I_{DAC}$ and the y-axis is $Q_{DAC}$. In many embodiments, the values can be the 12 bit DAC values: 0 to 4095. It can be beneficial to know that the gain of the RF and demodulation chain is such that the range of values is large enough to easily saturate the demodulation (indicated by very large output values from the ADC).

Figure 17B:
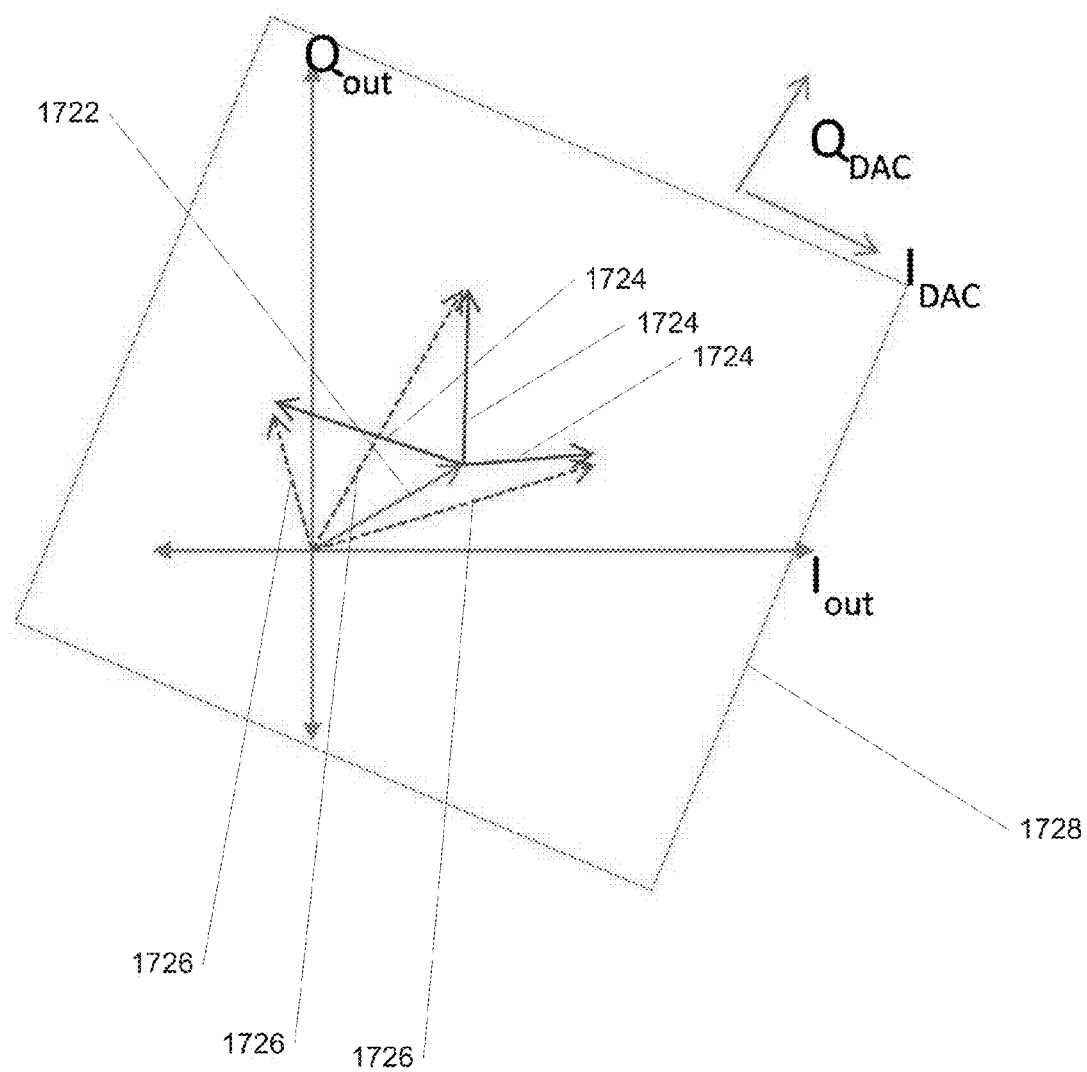

The receiver RF chain sums the antenna signal and the cancellation path, which can be viewed as a vector sum. A graph illustrating a vector sum in accordance with an embodiment of the invention is shown in FIG. 17B. The graph 1720 shows the input signal 1722 has a particular magnitude and phase, and the cancellation signal 1724 has a different magnitude and phase, with the sum being shown as a dashed line 1726. The cancellation box 1728 is tilted because there is a fixed phase shift (that varies with temperature and frequency) in the cancellation path, so for each calibration, the precise position and angle of the box is unknown. The cancellation vector can be anything within the box.

Figure 17C:
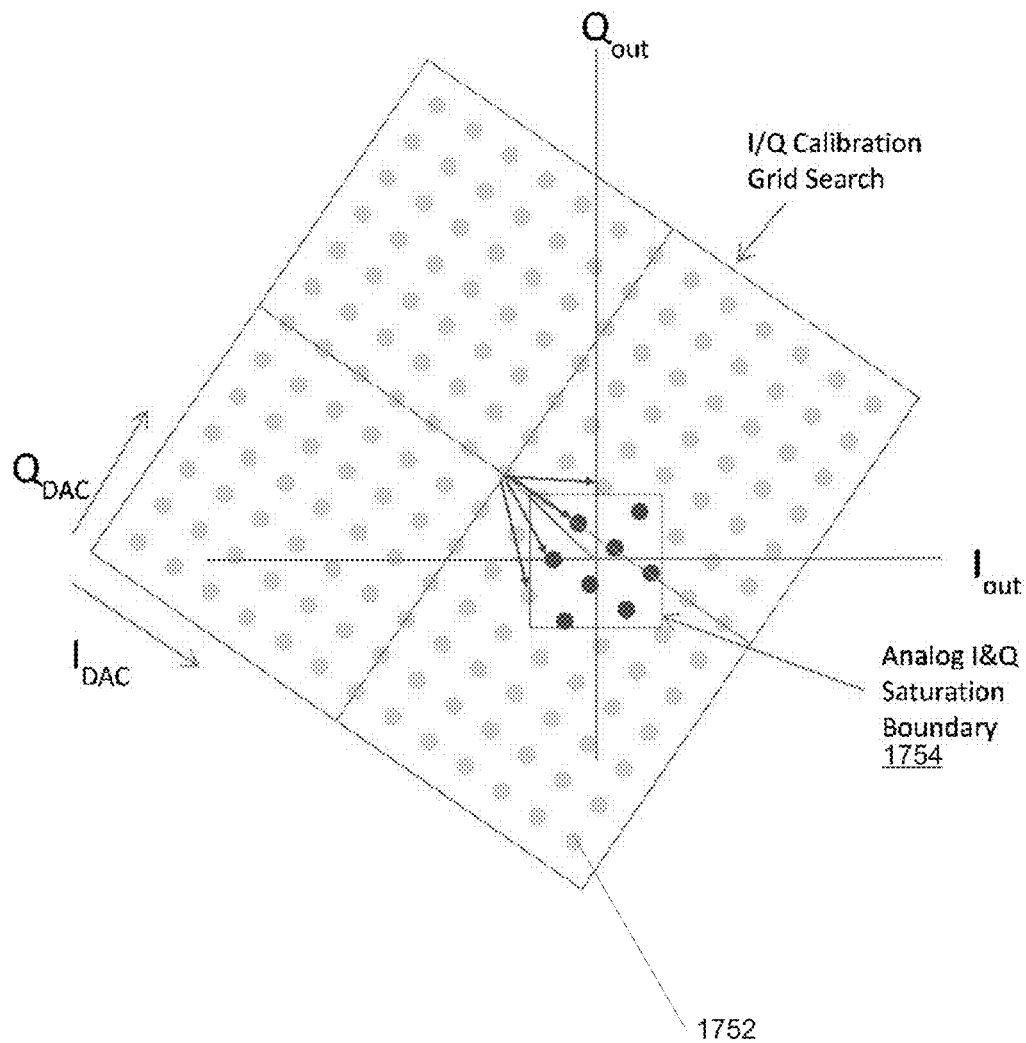

In various embodiments, the C command can perform a grid search, stepping $I_{DAC}$ and $Q_{DAC}$ through a set of values. A graph illustrating a calibration grid search in accordance with an embodiment of the invention is shown in FIG. 17C. The graph 1750 includes various dots 1752 within the box illustrating the set of values that $I_{DAC}$ and $Q_{DAC}$ steps through in performing a grid search. Typically, the process can remember which values do not cause the RF chain to be saturated, and keeps a list of the 16 entries which have the lowest magnitude. In several embodiments, the saturation range is indicated in the figure by a box 1754, and in this example, 8 $I_{DAC}/Q_{DAC}$ pairs do not saturate the receiver. In many embodiments, the text output from the calibration process can be an ASCII grid showing period for pairs where the receiver is saturated and asterisks for pairs where the receiver is within the linear range as illustrated in TABLE 2 below. Although, the best of the grid points is kept for further processing, the number and configuration of "non-saturated" points can be a valuable diagnostic tool. If there are NO non-saturated points, it indicates that either no calibration was possible (the hardware is broken), or that the gain is higher than expected (especially if only one or two grid points are non-saturated). Similarly, an excess of non-saturated grid points would indicate that the gain is too low, either in the cancellation path or in the receiver path. In some embodiments, the input and output values at the non-saturated grid points can be used to calculate the gain and offset of the cancellation path.

TABLE 2

Sample text output from
the calibration process illustrated in
FIG. 17C.

.............
.............
.............
.............
.............
.............
..........*...
.........***..
.........***..
..........*...
.............
.............
.............
.............

In performing a grid search for a calibration starting point, the coarse calibrate command C sets I/Q to all combinations of the values [300:300:3900] and measures the I/Q outputs and magnitudes. If the I/Q output value are inside the range [−250k,250k], indicating that it's not saturated (280k), the Iset and Qset values, and the outputs can be remembered. Typically there are 4-6 places where this is true, but the table holds up to 16 sets. If more "qualifying" values are found, one of the others with a higher magnitude is thrown out and replaced. A large number of valid points usually indicates that the gain in the RF path is low, there is no power applied to the receiver board (i.e. the P command has not been sent), or insufficient RF power is coming in on the reference input. At the end of the grid search process, the (up to) top 16 candidates are printed, and the selected values with the lowest magnitude are loaded into the DACs, preparing for the gradient refinement. As a practical matter, the gradient refinement probably is not needed; experience with the first radar indicated that as long as the analog values are in the middle half of the ADC range, we have enough dynamic range to process the signals. It may be noteworthy that with NO RF signal being received on the antenna, a good calibration should still be possible, since the cancellation path is typically 10 dB larger than the largest received signal, and is sufficient to saturate the RF chain. The ability to get a good calibration is a good test of the function of a receive RF module.

In performing a stepwise gradient optimization with the command D, given the current I/Q starting point, a step wise gradient optimization process can used to drive the Iout/Qout as low as possible. In many embodiments, the process includes starting in the present I/Q place, move a step in each of the 4 directions (+I,−I,+Q,−Q). In several embodiments, the step size starts at 64. If any of the steps is lower than the present value, then repeat the process. When the 4 steps are all bigger than where we are now (e.g. we're near the minimum), cut the stepsize in half. Repeat the process, each time, until the stepsize gets to 2.

As a note on the calibration process, there can be a tradeoff between the step size in C "grid search" command vs step size in D "tune" command. A smaller step in the grid search will make that take longer, but the fine tune should take less time. There is also a tradeoff of what the search termination criteria should be. It may be that stopping at a step size of 4 or 8 might be as effective. With no RF input, but LO signal from a transmitter provided, running the complete calibration, a module converged to the following I/Q values over about 10 seconds (where the small changes indicate some residual thermal effects):
I,Q: 2228 2244
I,Q: 2226 2242
I,Q: 2224 2240
Repeating the calibration 40 seconds later
I,Q: 2222 2238
The sampled output from the M command is: 2485 1823 0.01
and a couple minutes later
I,Q: 2204 2236
M output: −3289 −2875 0.00

In context, 1 DAC LSB is about 500 ADC LSB, so converging to a few hundred ADC LSB is <1 DAC LSB. The calibration routines call iqshort( ) to make the measurement and it returns sum(1800 samples)/180 or 10*actual value: −328.9, −287.5 here. The magnitude is relative to 2.0, so 0.01 is very small. A host PC should track the results of these calibration searches, to identify long term calibration shifts, and also for diagnosis of problems; e.g. a sudden change may indicate a failed component.

Figure 18:
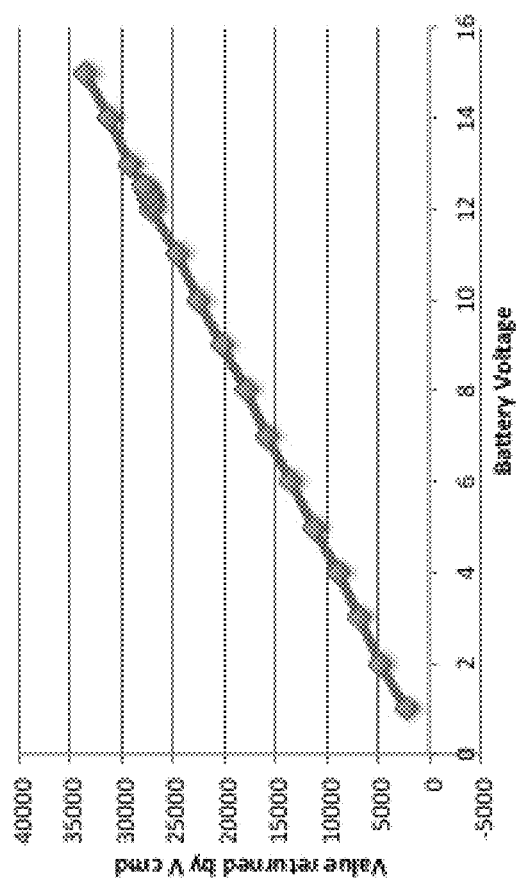
FIG. 18 is a chart illustrating a sample voltage calibration in accordance with an embodiment of the invention.

In many embodiments, the voltage calibration data can be analyzed. A chart illustrating voltage calibration data from a single unit in accordance with an embodiment of the invention is illustrated in FIG. 18. A 12V voltage can be measured by Analog input 2 (A2) using a standard readAnalog( ) call. The input is derived from a voltage divider (100k over 10k, so approximately 1:11) that brings the voltage down to the 0-2.67 V range of the ADC. In several embodiments, the reference voltage for the ADC can be derived from a voltage divider formed by the series 470 ohm resistor on the teensy between the 3.3 Vdd and Vref, and a series pair of 1 K resistors from Vref to ground providing the midpoint reference for the analog buffers. This puts Vref at 2/2.47*3.3V or 2.67V (subject to the tolerances of the resistors, nominally 5%). Table 3 (illustrated below) gives some nominal values.

TABLE 3

| Sample Values returned by V command | |
|---|---|
| Vbatt | V cmd |
| 10 | 22297 |
| 10.5 | 23412 |
| 11 | 24526 |
| 11.5 | 25641 |
| 12 | 26756 |
| 12.5 | 27871 |
| 13 | 28986 |
| 13.5 | 30101 |
| 14 | 31215 |
| 14.5 | 32330 |

Setup processes (i.e. initialization) can be performed using the Arduino setup( ) routine. In many embodiments, initialization includes setting up the ADC interface where the voltage reference is set to external (approximately 2.67 V), the resolution is set to 16 bits, and the averaging is set to use a single sample. Further, the serial port can be initialized to 9600 bps, although in the teensyduino environment which uses the USB to emulate the serial port, the emulated port runs at full USB speed. In addition, the pin used to control the RF power converter can be setup as an output and initialized to low (disabling RF power). Although specific calibration and initialization processes are discussed above with respect to FIGS. 17A-18 and Tables 2-3, any of a variety of calibration and initialization processes as appropriate to the requirements of a specific application can be utilized in accordance with embodiments of the invention. Timing test results in accordance with embodiments of the invention are discussed further below.

Synchronization and Timing Test Results

As discussed above, sensor modules can include various interfaces for connectivity. Further, various transmitter and receiver units can be synched by staggering operation times, where multiple antennas can provide results for comparisons. In addition, a modular approach lends itself to scalability, repackaging and easier debugging. In various embodiments, multiple sensor modules can even be part of a single system taking commands from a single central host PC. Thus, it may be beneficial to analyze timing measurements of the code running on the microcontroller.

An interface build was modified using 3 output pins to indicate when various sections of the code were executing. The pins were set up to measure the following events:
1) the time in the Interrupt Service Routine (ISR) that runs at 50 kHz collecting the raw IQ samples and generating decimated samples at 1 kHz;
2) the time spent in the "data ready" routine which runs at 200 Hz generating the final filtered and decimated output transmitted over the USB serial port; and
3) the time spent in the FIR filtering routing.

In many embodiments, the ISR can consume about 60% of the processor resources, and the rest of the processing can consume about 1% of the processor resources. The relatively small amount of time spent processing the 1 kHz sampled data implies that significantly more processing could be done if needed.

Figure 19:
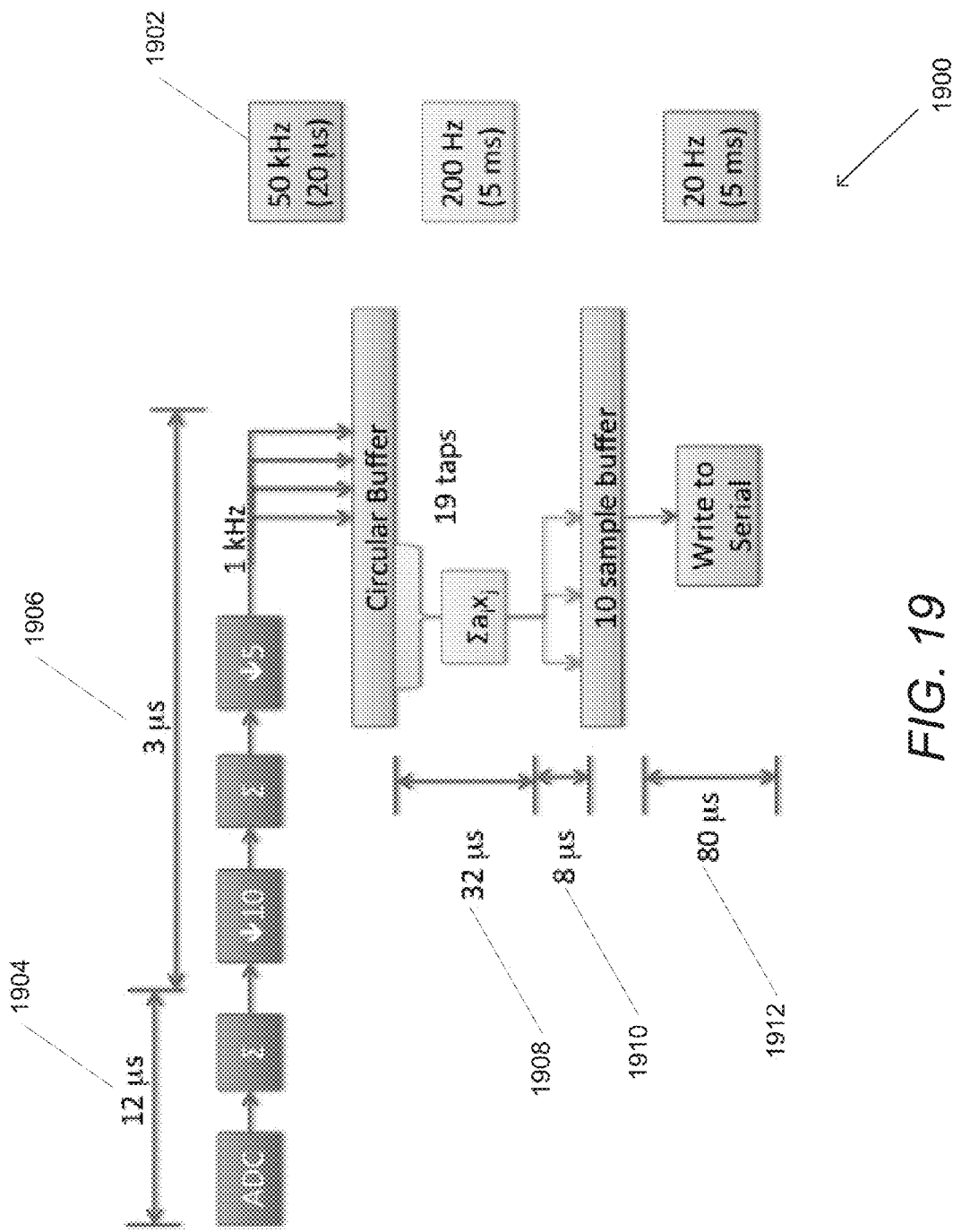
FIG. 19 is chart illustrating timing test results in accordance with an embodiment of the invention.

The results of the time measurements in accordance with an embodiment of the invention are illustrated in FIG. 19. In measuring the 50 kHz Interrupt Service Routine (ISR) a bit was set on entry and exit of "ReadIQ" which is the interrupt routine that reads the I and Q values and loads the CIC decimators. As the data results 1900 illustrate, it runs every 20 microseconds, corresponding to the 50 kHz sample rate 1902. The time spent in the routine varies according to the time spent in the decimation 1904 (e.g. every 10 iterations, it has to generate an output for the first stage, and then every 50 it has to generate the output for the second stage which appear to take approximately 12 microseconds (plus another 3 microseconds sometimes 1906). Out of 20 microseconds, the ISR is taking 60% of the processor. In various embodiments, benchmarking showed that the maximum rate of a bit more than 100 kHz was possible with I/Q samples of 16 bits, so the current 60% utilization at 50 kHz seems consistent.

In measuring the 200 Hz sample processing, time is measured related to how long it spends inside the "data ready" logic in loop( ) which runs every 5 times the CIC decimator chain kicks out a sample. In various embodiments, when the flag is set, the FIR filter processes the last 19 samples and loads the USB output buffer with an encoded sample. Every 10 I/Q pairs (that is, every 50 milliseconds), this routine sends a 64 byte buffer out to the USB interface. The test results indicate that it takes approximately 40 microseconds to do the FIR filter and store the encoded values. The actual FIR 1908 takes 32 microseconds, so loading the buffer and other overhead 1910 is about 8 microseconds. Then, it takes 80 microseconds to transfer a buffer to the USB 1912 (from there, it's handled by a hardware engine in the microcontroller). Since this loop runs at 200 Hz, it doesn't take very much processor resources. For example, at 32 microseconds*200 samples=6.4 ms; 8 microseconds*200 samples=1.6 ms; 80 microseconds*20 buffers=1.6 ms; for a total time in 1 second=9.6 ms. This is less than 1% of the processor's capacity, so it may be beneficial to perform additional functions such as (but not limited to) various data validations. In addition, the time spent in the FIR filtering routine was measured. In many embodiments, the FIR filter (19 taps) runs at 200 Hz, and takes 32 microseconds to calculate. Most likely, the longer delay is when the IQ sampling (which takes 12 microseconds) happens to occur during the FIR calculation. Although specific timing test results are discussed above with respect to FIG. 19, any of variety of timing test and timing test results can be utilized in accordance with embodiments of the invention.

While the above description contains many specific embodiments of the invention, these should not be construed as limitations on the scope of the invention, but rather as an example of one embodiment thereof. It is therefore to be understood that the present invention may be practiced otherwise than specifically described, without departing from the scope and spirit of the present invention. Thus, embodiments of the present invention should be considered in all respects as illustrative and not restrictive.

What is claimed is:

1. An integrated microwave sensor module comprising:
a transmitter unit comprising a variable frequency microwave source connected to at least one transmitter unit amplifier, where:
the variable frequency microwave source is configured to generate at least one continuous wave ("CW") transmit signal based upon at least one frequency control signal received from a microcontroller unit; and
the at least one transmitter unit amplifier is configured to receive and amplify the at least one CW transit signal;
a receiver unit configured to receive at least one return signal and utilize a cancellation path to cancel contributions to the return signal that are not the result of reflections from a target comprising a vector modulator, a combiner, a vector demodulator, and at least one receiver unit amplifier, where:
the vector modulator is configured to receive at least one cancellation path control signal from the microcontroller unit, sample the at least one CW transmit signal, and adjust an amplitude and phase of the sampled CW transmit signal based upon the at least one cancellation path control signal;
the combiner is configured to receive the adjusted transmit signal and combine it with the at least one return signal;
the at least one receiver unit amplifier is configured to amplify the combined signal; and
the vector demodulator is configured to receive the amplified combined signal, sample the at least one CW transmit signal, and generate two baseband signals by coherently demodulating the amplified combined signal using the sampled CW transmit signal;
a microcontroller unit configured to communicate with the transmitter and receiver units comprising:
a processor;
a memory containing a microcontroller application, wherein the microcontroller application configures the processor to:
generate at least one frequency control signal, wherein the at least one frequency control signal can configure the transmitter unit to generate least one CW transmit signal having a plurality of frequencies;
generate at least one cancellation path control signal, wherein the at least one cancellation path control signal can configure the receiver unit to automatically adjust the cancellation path in real time;
receive at least one demodulated signal from the receiver unit;
digitize the at least one demodulated signal; and
update the at least one frequency control and cancellation path control signals based upon the received at least one demodulated signal.

2. The integrated microwave sensor module of claim 1, wherein the variable frequency microwave source is a voltage controlled oscillator.

3. The integrated microwave sensor module of claim 1, wherein the at least one transmitter unit amplifier is connected to at least one transmit antenna configured to propagate at least one beam using the amplified CW transmit signal set at a plurality of frequencies.

4. The integrated microwave sensor module of claim 3, wherein the at least one return signal is associated with reflections from objects of the at least one beam, where the return signal comprises at least one signal component having a static phase associated with reflections from nonmoving objects and at least one signal component having time varying phase associated with at least one target.

5. The integrated microwave sensor module of claim 4, wherein the microcontroller application further configures the processor to automatically adjust cancellation paths associated with each of the plurality of frequencies.

6. The integrated microwave sensor module of claim 1, wherein the microcontroller unit further comprises at least one digital-to-analog converter for processing the at least one transmitter frequency control signal.

7. The integrated microwave sensor module of claim 1, wherein the microcontroller unit further comprises a plurality of digital-to-analog converters for processing the at least one cancellation path control signal.

8. The integrated microwave sensor module of claim 1, wherein receiver unit further comprises a low pass filter to filter the demodulated signal.

9. The integrated microwave sensor module of claim 1, wherein the microcontroller unit further comprises a plurality of analog-to-digital converters that digitizes the at least one demodulated signal received from the receiver unit.

10. The integrated microwave sensor module of claim 1, wherein the microcontroller unit is connected to a host computer.

11. The integrated microwave sensor module of claim 1, wherein the microcontroller unit further comprises a temperature sensor configured to take a temperature measurement related to the sensor module.

12. The integrated microwave sensor module of claim 11, wherein the microcontroller application further configures the processor to generate an updated frequency control signal based upon the temperature measurement.

13. The integrated microwave sensor module of claim 11, wherein the microcontroller application further configures the processor to generate an updated cancellation path control signal based upon the temperature measurement, wherein the temperature measurement can provide an a priori starting point for adjusting the cancellation path.

14. The integrated microwave sensor module of claim 1, wherein the microcontroller application further configures the processor to validate the demodulated signals and format for further processing.

15. The integrated microwave sensor module of claim 14, wherein the microcontroller application further configures the processor to provide range resolution by processing time and frequency measurements.

16. The integrated microwave sensor module of claim 1, wherein the transmitter unit is implemented on a first printed-circuit-board ("PCB"), the receiver unit is implemented on a second PCB, and the microcontroller unit is implemented on a third PCB.

17. The integrated microwave sensor module of claim 1, wherein the transmitter and receiver units are separate and synchronized.

18. The integrated microwave sensor module of claim 1, wherein the integrated microwave sensor module is synchronized with another integrated microwave sensor module.

19. The integrated microwave sensor module of claim 1, further comprising N transmitter units, M receive antennas, and N×M receiver units to simultaneously processes multiple frequencies.

20. The integrated microwave sensor module of claim 1, wherein the vector modulator can be an alternate discrete implementation comprising a quadrature hybrid coupler, a first and second discrete mixers, and a power combiner.

21. The integrated microwave sensor module of claim 20, wherein the quadrature hybrid coupler receives a sampled CW transmit signal from the transmitter unit and splits the received sampled CW transmit signal into a first and second split signals that are 90 degrees apart in phase.

22. The integrated microwave sensor module of claim 21, wherein the first discrete mixer is configured to receive the first split signal and a first input control signal and output a first mixer signal.

23. The integrated microwave sensor module of claim 22, wherein the second discrete mixer is configured to receive the second split signal and a second input control signal and output a second mixer signal.

24. The integrated microwave sensor module of claim 23, wherein the first and second mixer signals are combined using the power combiner to generate a cancellation signal.

25. An integrated microwave sensor module comprising:
a transmitter unit comprising a voltage controller oscillator ("VCO") connected to at least one transmitter unit amplifier, where:
the VCO is configured to generate at least one continuous wave ("CW") transmit signal based upon at least one frequency control signal received from a microcontroller unit;
the at least one transmitter unit amplifier is configured to receive and amplify the at least one CW transit signal; and
wherein the at least one transmitter unit amplifier is connected to at least one transmit antenna configured to propagate at least one beam using the amplified CW transmit signal set at a plurality of frequencies based upon the at least one frequency control signal;
a receiver unit configured to receive at least one return signal and utilize a cancellation path to cancel contributions to the return signal that are not the result of reflections from a target comprising a vector modulator, a combiner, a vector demodulator, and at least one receiver unit amplifier, where:
the vector modulator is configured to receive at least one cancellation path control signal from the microcontroller unit, sample the at least one CW transmit signal, and adjust an amplitude and phase of the sampled CW transmit signal based upon the at least one cancellation path control signal;
the combiner is configured to receive the adjusted transmit signal and combine it with the at least one return signal;
the at least one receiver unit amplifier is configured to amplify the combined signal;
the vector demodulator is configured to receive the amplified combined signal, sample the at least one CW transmit signal, and generate two baseband signals by coherently demodulating the amplified combined signal using the sampled CW transmit signal; and
wherein the at least one return signal is associated with reflections from objects of the at least one beam, where the return signal comprises at least one signal component having a static phase associated with reflections from nonmoving objects and at least one signal component having time varying phase associated with at least one target;
a microcontroller unit configured to communicate with the transmitter and receiver units comprising:
a processor;
a memory containing a microcontroller application, wherein the microcontroller application configures the processor to:
generate at least one frequency control signal, wherein the at least one frequency control signal can configure the transmitter unit to generate least one CW transmit signal having a plurality of frequencies;
generate at least one cancellation path control signal, wherein the at least one cancellation path control signal can configure the receiver unit to automatically adjust the cancellation path in real time;

receive at least one demodulated signal from the receiver unit;

digitize the at least one demodulated signal; and update the at least one frequency control and cancellation path control signals based upon the received at least one demodulated signal;

at least one digital-to-analog converter for processing the at least one transmitter frequency control signal;

a plurality of digital-to-analog converters for processing the at least one cancellation path control signal; and a plurality of analog-to-digital converters that digitizes the at least one demodulated signal received from the receiver unit.

\* \* \* \* \*